(12) United States Patent
Taguchi et al.

(10) Patent No.: US 9,913,578 B2
(45) Date of Patent: Mar. 13, 2018

(54) EYE GAZE DETECTING DEVICE AND EYE GAZE DETECTION METHOD

(71) Applicant: FUJITSU LIMITED, Kawasaki-shi, Kanagawa (JP)

(72) Inventors: Akinori Taguchi, Kawasaki (JP); Satoshi Nakashima, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 14/836,284

(22) Filed: Aug. 26, 2015

(65) Prior Publication Data

US 2016/0095511 A1 Apr. 7, 2016

(30) Foreign Application Priority Data

Oct. 2, 2014 (JP) .................................. 2014-204274

(51) Int. Cl.
*A61B 3/00* (2006.01)
*G06F 3/01* (2006.01)
*A61B 3/113* (2006.01)
*A61B 3/14* (2006.01)
*G06K 9/00* (2006.01)

(52) U.S. Cl.
CPC ............ *A61B 3/0025* (2013.01); *A61B 3/113* (2013.01); *A61B 3/14* (2013.01); *G06F 3/013* (2013.01); *G06K 9/00597* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,220,926 B2* | 7/2012 | Blixt | ...................... | A61B 3/113 351/209 |
| 8,885,882 B1* | 11/2014 | Yin | .......................... | G06F 3/00 382/103 |
| 2003/0098954 A1* | 5/2003 | Amir | ...................... | A61B 3/113 351/210 |
| 2003/0123027 A1* | 7/2003 | Amir | ...................... | A61B 3/113 351/209 |

(Continued)

FOREIGN PATENT DOCUMENTS

| | | |
|---|---|---|
| EP | 2709060 A1 | 3/2014 |
| JP | 11-76165 | 3/1999 |

(Continued)

OTHER PUBLICATIONS

Extended European Search Report dated Mar. 1, 2016 in related European Application No. 15182720.1.

(Continued)

*Primary Examiner* — Tsung-Yin Tsai
(74) *Attorney, Agent, or Firm* — Staas & Halsey LLP

(57) ABSTRACT

An eye gaze detecting device includes: a memory configured to store position information regarding a specific position where a specific object is located; and a processor coupled to the memory and configured to: identify an eye gaze position regarding the subject in an image for each of a plurality of images including the image, and calculate a correction value based on the position information and a plurality of eye gaze positions including the eye gaze position, the correction value causing the plurality of eye gaze positions to match the specific position.

10 Claims, 30 Drawing Sheets

(56) References Cited

U.S. PATENT DOCUMENTS

| | | | | |
|---|---|---|---|---|
| 2009/0304232 A1* | 12/2009 | Tsukizawa | ............ | A61B 3/113 382/103 |
| 2011/0228975 A1* | 9/2011 | Hennessey | ............ | A61B 3/113 382/103 |
| 2014/0085198 A1* | 3/2014 | Jahnke | ............ | G06F 3/013 345/157 |
| 2015/0278599 A1* | 10/2015 | Zhang | ............ | G06K 9/00604 348/78 |

FOREIGN PATENT DOCUMENTS

| | | |
|---|---|---|
| JP | 2011-217764 | 11/2011 |
| JP | 2013-524390 | 6/2013 |
| WO | 2011/130594 A1 | 10/2011 |
| WO | 2013/059940 A1 | 5/2013 |
| WO | WO 2013059940 A1 * | 5/2013 ............ A61B 3/113 |

OTHER PUBLICATIONS

Roberto Valenti et al., "What are you looking at? Improving Visual Gaze Estimation by Saliency", International Journal of Computer Vision, Kluwer Academic Publishers, Dec. 17, 2011, vol. 98, No. 3, pp. 324-334.

Canadian Office Action dated Jul. 11, 2016 in Canadian Application No. 2,902,684.

Extended European Search Report dated Aug. 10, 2016 in related European Application No. 16168533.4.

Australian Office Action dated Dec. 2, 2016 in corresponding Australian Patent Application No. 2015221480.

Office Action of Canadian Patent Application No. 2902684 dated Mar. 10, 2017.

Australian Office Action dated Aug. 9, 2016 in Australian Application No. 2015221480.

* cited by examiner

FIG. 4

| COMMODITY | UPPER LEFT POSITION | LOWER RIGHT POSITION |
|---|---|---|
| COMMODITY C1 | (x1,y1) | (x1+a,y1+b) |
| COMMODITY C2 | (x2,y2) | (x2+a,y2+b) |
| ⋮ | ⋮ | ⋮ |

FIG. 7

| PUPILLARY DISTANCE | COMMODITY-USER DISTANCE |
|---|---|
| 460 | 40 |
| 300 | 60 |
| 230 | 80 |
| 180 | 100 |
| 150 | 120 |

FIG. 8

| COMMODITY-USER DISTANCE | CATEGORY |
|---|---|
| ~50 | T1 |
| 50~100 | T2 |
| 100~ | T3 |

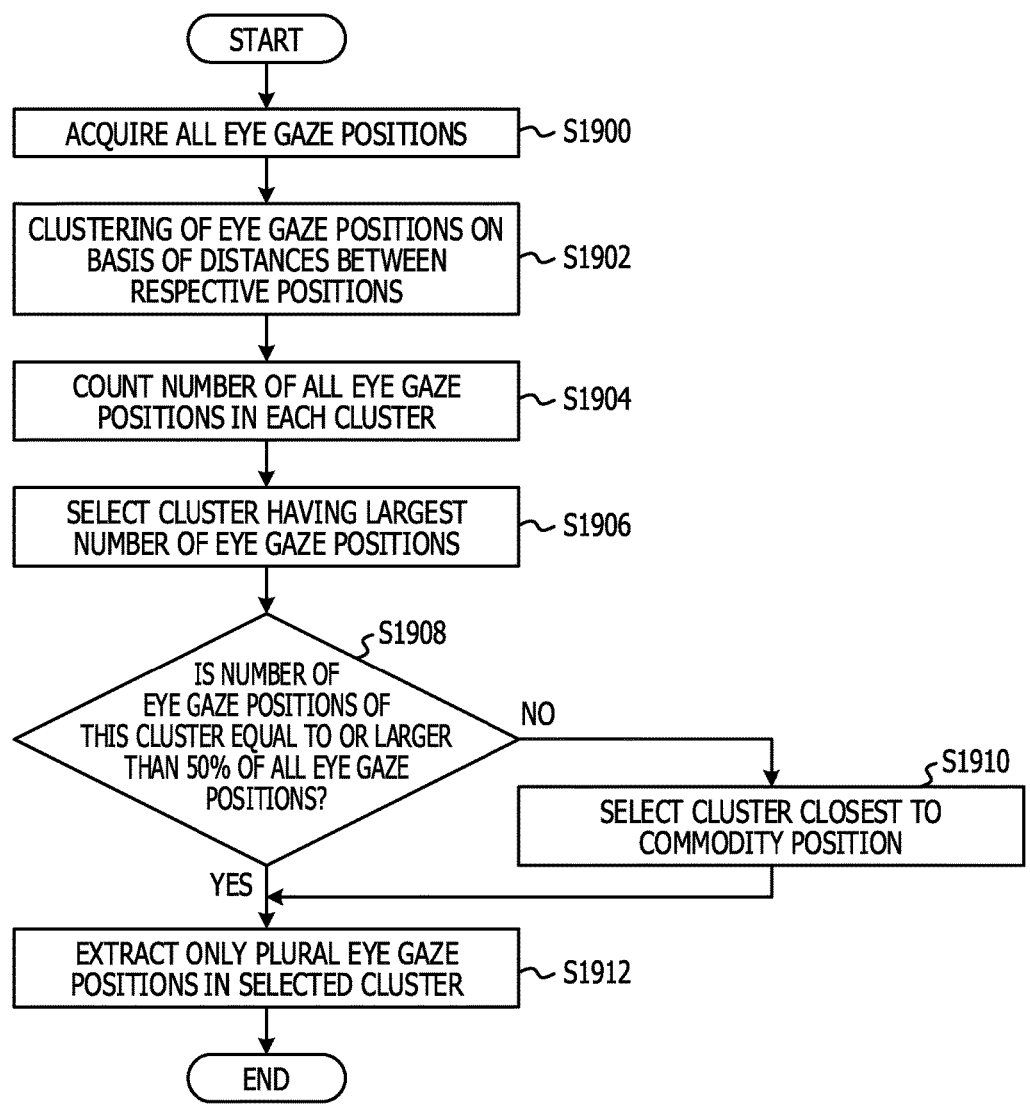

FIG. 22

| COMMODITY NAME | COMMODITY POSITION (BASED ON SENSOR) |
|---|---|
| C1 | (0,0,0) |
| C2 | (x2,0,0) |
| C3 | (-x3,0,0) |

FIG. 30

|  | C1 | C2 |
|---|---|---|
| Q1 | D11 | D12 |
| A2 | D21 | D22 |

EYE GAZE DETECTING DEVICE AND EYE GAZE DETECTION METHOD

CROSS-REFERENCE TO RELATED APPLICATION

This application is based upon and claims the benefit of priority of the prior Japanese Patent Application No. 2014-204274, filed on Oct. 2, 2014, the entire contents of which are incorporated herein by reference.

FIELD

Techniques disclosed in the present embodiments are related to techniques for detecting the position of the eye gaze.

BACKGROUND

A correction value calculating device that calculates a correction value for correcting an error in the eye gaze associated with the individual difference of an object person in detection of the eye gaze is known (for example refer to Patent Document 1). This correction value calculating device calculates the correction value on the basis of a first eye gaze vector that is calculated on the basis of a shot image of an eye of a subject and is directed from the eye toward a screen of a display device and a second eye gaze vector toward a point of gaze at which the subject is gazing, decided on the basis of the feature on a displayed image. For example, these techniques are disclosed in Japanese Laid-open Patent Publication No. 2011-217764, Japanese Laid-open Patent Publication No. 11-76165, and Japanese National Publication of International Patent Application No. 2013-524390.

SUMMARY

According to an aspect of the invention, an eye gaze detecting device includes: a memory configured to store position information regarding a specific position where a specific object is located; and a processor coupled to the memory and configured to: identify an eye gaze position regarding the subject in an image for each of a plurality of images including the image, and calculate a correction value based on the position information and a plurality of eye gaze positions including the eye gaze position, the correction value causing the plurality of eye gaze positions to match the specific position.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 4 is a (first) explanatory diagram of a commodity position database 14.

FIG. 7 is a diagram illustrating one example of relationship between pupillary distance and commodity-user distance.

FIG. 8 is a diagram illustrating one example of relationship between the commodity-user distance and a category.

FIG. 19 is a flowchart illustrating one example of the eye gaze position selection processing executed by a correction value calculating unit 12.

FIG. 22 is a diagram illustrating one example of data in the commodity position database 14 used in the example illustrated in FIG. 21.

FIG. 30 is a table diagram representing respective distances.

DESCRIPTION OF EMBODIMENTS

The correction value calculating device calculates the correction value in real time by using the first eye gaze vector calculated on the basis of a shot image of a certain timing. Therefore, it is difficult to calculate the correction value with high accuracy. For example, if an object person looks at the point of gaze decided on the basis of the feature on the displayed image after taking a survey of the screen of the display device globally, many of the plural eye gaze positions obtained during the survey are eye gaze positions when the object person is not gazing at the point of gaze based on the feature on the displayed image. Thus, with the configuration to calculate the correction value by individually using such eye gaze positions, it is difficult to calculate the correction value with high accuracy.

Therefore, the disclosed techniques intend to calculate a correction value with high accuracy.

The respective embodiments will be described in detail below with reference to the accompanying drawings.

Figure 1:
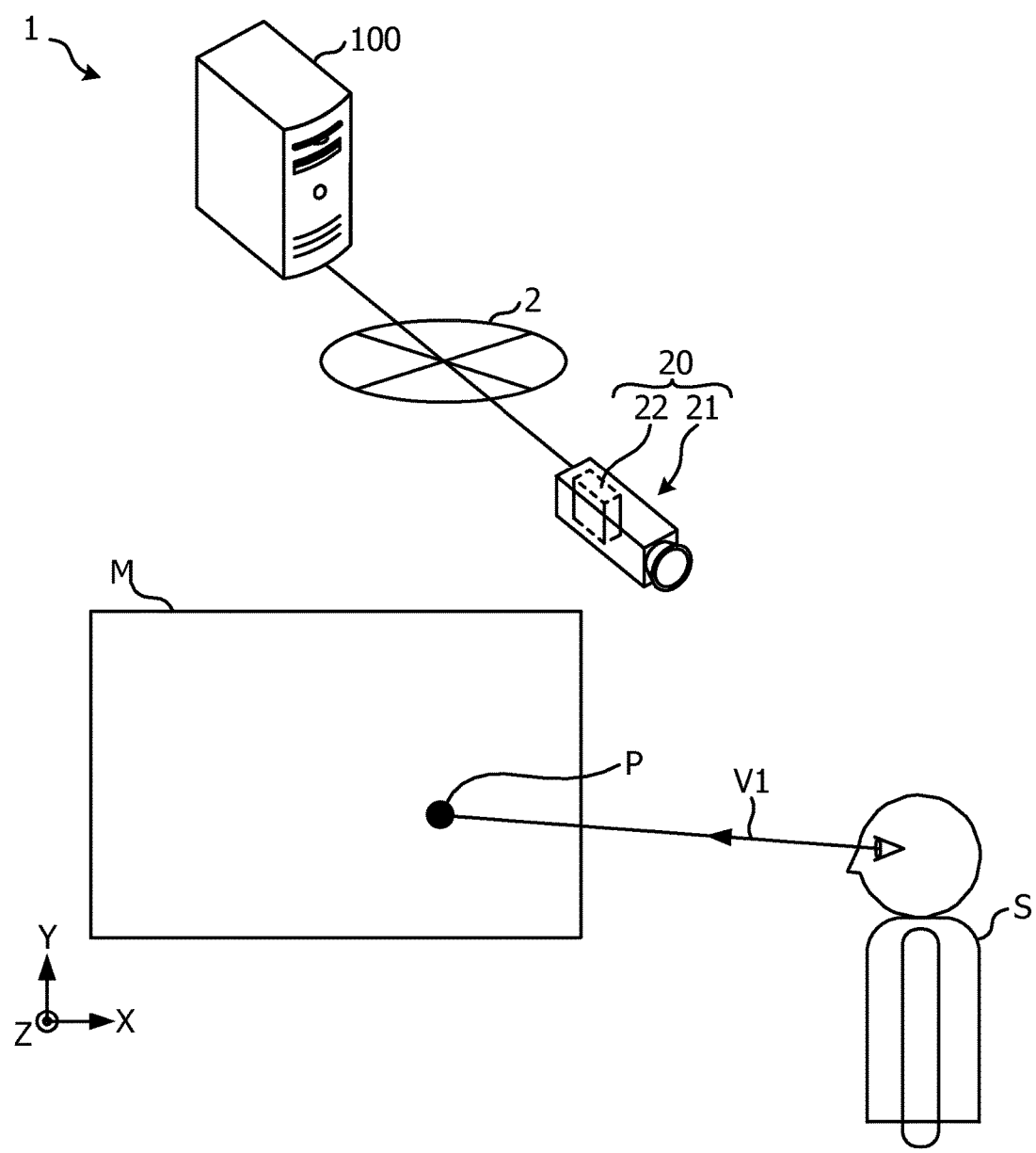
FIG. 1 is a diagram illustrating one example of an eye gaze position detecting system 1 to which an eye gaze position detecting device is applied.

FIG. 1 is a diagram illustrating one example of an eye gaze position detecting system 1 to which an eye gaze position detecting device is applied.

The eye gaze position detecting system 1 includes an eye gaze sensor 20 and an eye gaze position detecting device 100. The eye gaze position detecting device 100 is communicably coupled to the eye gaze sensor 20 in a wired or wireless manner.

The eye gaze sensor 20 includes a camera 21 and an eye gaze vector calculating device 22.

The camera 21 acquires a shot image of an eye of a user S (one example of subject). The camera 21 may include an imaging element of an arbitrary type. For example, the camera 21 may be a comparatively inexpensive complementary metal-oxide-semiconductor (CMOS) camera.

The eye gaze vector calculating device 22 calculates an eye gaze vector V1 of the user S on the basis of the shot image of the camera 21. The calculation method of the eye gaze vector V1 of the user S is arbitrary. The calculation method of the eye gaze vector V1 of the user S may be a method disclosed in Japanese Laid-open Patent Publication No. 2011-217764 for example. Furthermore, the detection method of the eye gaze direction (eye gaze vector V1) may be a corneal reflection method in which a pupil and corneal reflection are sensed and the eye gaze direction is calculated from the positional relationship between them. In this case, the eye gaze sensor 20 includes a near-infrared light-emitting diode (LED). This method, in which near-infrared light by the near-infrared LED is made to impinge on the face of the user S, utilizes a characteristic that the position of the corneal reflection is not affected by the eye gaze direction although the position of the pupil changes depending on the eye gaze direction. In the case of making the near-infrared light by the near-infrared LED impinge on the face, the corneal reflection serving as a reference point is caused in the eye and thus the measurement accuracy is improved compared with a method of carrying out measurement from only a camera.

The eye gaze vector calculating device 22 may be included in the camera 21 as a built-in device as illustrated in FIG. 1. However, in another embodiment, the eye gaze vector calculating device 22 may be coupled to the camera 21 and the eye gaze position detecting device 100 via a network 2 for example. Furthermore, the eye gaze vector calculating device 22 may be embedded in the eye gaze position detecting device 100. Alternatively, part or all of the functions of the eye gaze position detecting device 100 may be incorporated in the camera 21.

The eye gaze position detecting device 100 calculates a correction value for correcting an eye gaze position P detected by the eye gaze sensor 20. Calculation methods of the correction value will be described later.

Figure 2:
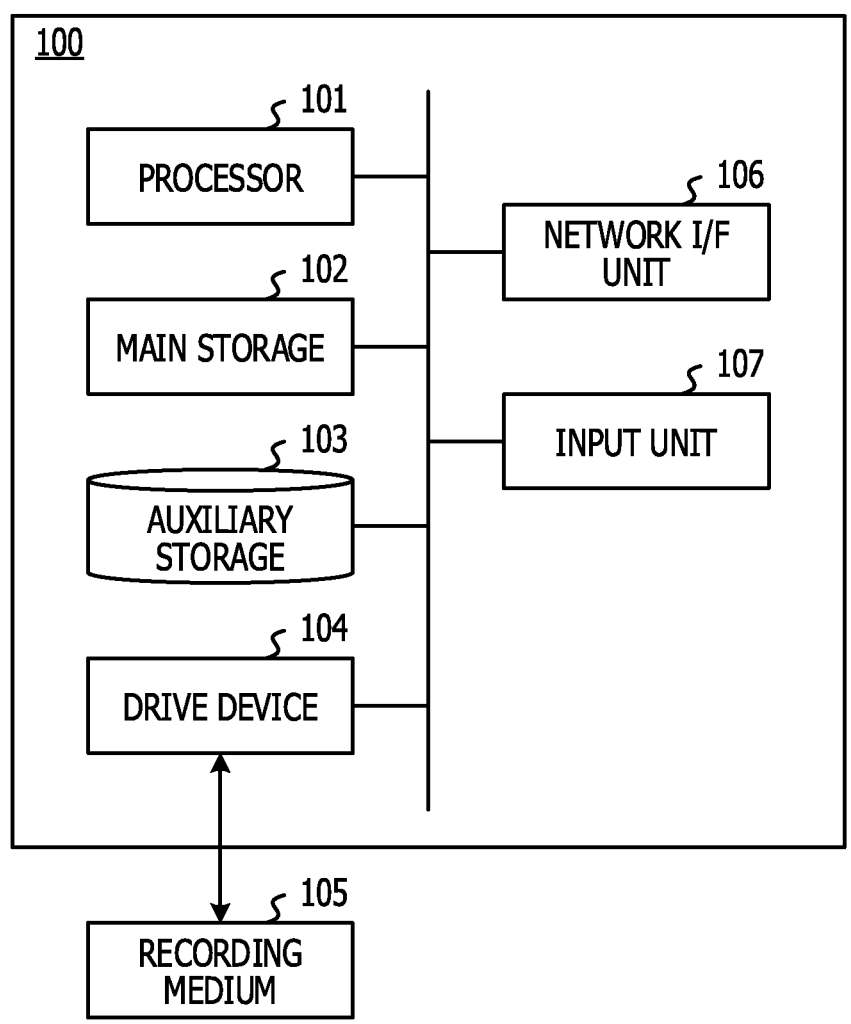
FIG. 2 is a diagram illustrating one example of a hardware configuration of an eye gaze position detecting device 100.

FIG. 2 is a diagram illustrating one example of a hardware configuration of the eye gaze position detecting device 100.

The eye gaze position detecting device 100 is implemented by a computer for example. In the example illustrated in FIG. 2, the eye gaze position detecting device 100 includes a processor 101, a main storage 102, an auxiliary storage 103, a drive device 104, a network I/F unit 106, and an input unit 107.

The processor 101 is an arithmetic device that executes programs stored in the main storage 102 and the auxiliary storage 103. The processor 101 receives data from the input unit 107 or a storage device to perform arithmetic operation and processing on the data and then output the resulting data to the storage device or the like.

The main storage 102 is a read only memory (ROM), a random access memory (RAM), and so forth. The main storage 102 is a storage device that stores or temporarily saves programs such as an operating system (OS) that is basic software executed by the processor 101 and application software and data.

The auxiliary storage 103 is a hard disk drive (HDD) or the like and is a storage device that stores data relating to the application software and so forth.

The drive device 104 reads out a program from a recording medium 105, e.g. a flexible disk, and installs the program on a storage device.

The recording medium 105 stores a given program. The program stored in this recording medium 105 is installed on the eye gaze position detecting device 100 via the drive device 104. The installed given program becomes executable by the eye gaze position detecting device 100.

The network I/F unit 106 is an interface between the eye gaze position detecting device 100 and peripheral equipment that is coupled via a network constructed by data transmission lines such as wired and/or wireless lines and has a communication function.

The input unit 107 includes a keyboard including cursor keys, numeric input keys, and various kinds of function keys, a mouse, a touch pad, etc.

In the example illustrated in FIG. 2, various kinds of processing and so forth to be described below can be implemented by making the eye gaze position detecting device 100 execute a program. Furthermore, it is also possible to record a program in the recording medium 105 and make the eye gaze position detecting device 100 read the recording medium 105 in which this program is recorded and implement the various kinds of processing and so forth to be described below. As the recording medium 105, recording media of various types can be used. For example, the recording medium 105 may be a recording medium in which information is recorded optically, electrically, or magnetically, such as a compact disc (CD)-ROM, a flexible disk, or a magneto-optical disk, or a semiconductor memory in which information is electrically recorded, such as a ROM or a flash memory, or the like. Carrier waves are not included in the recording medium 105.

Figure 3:
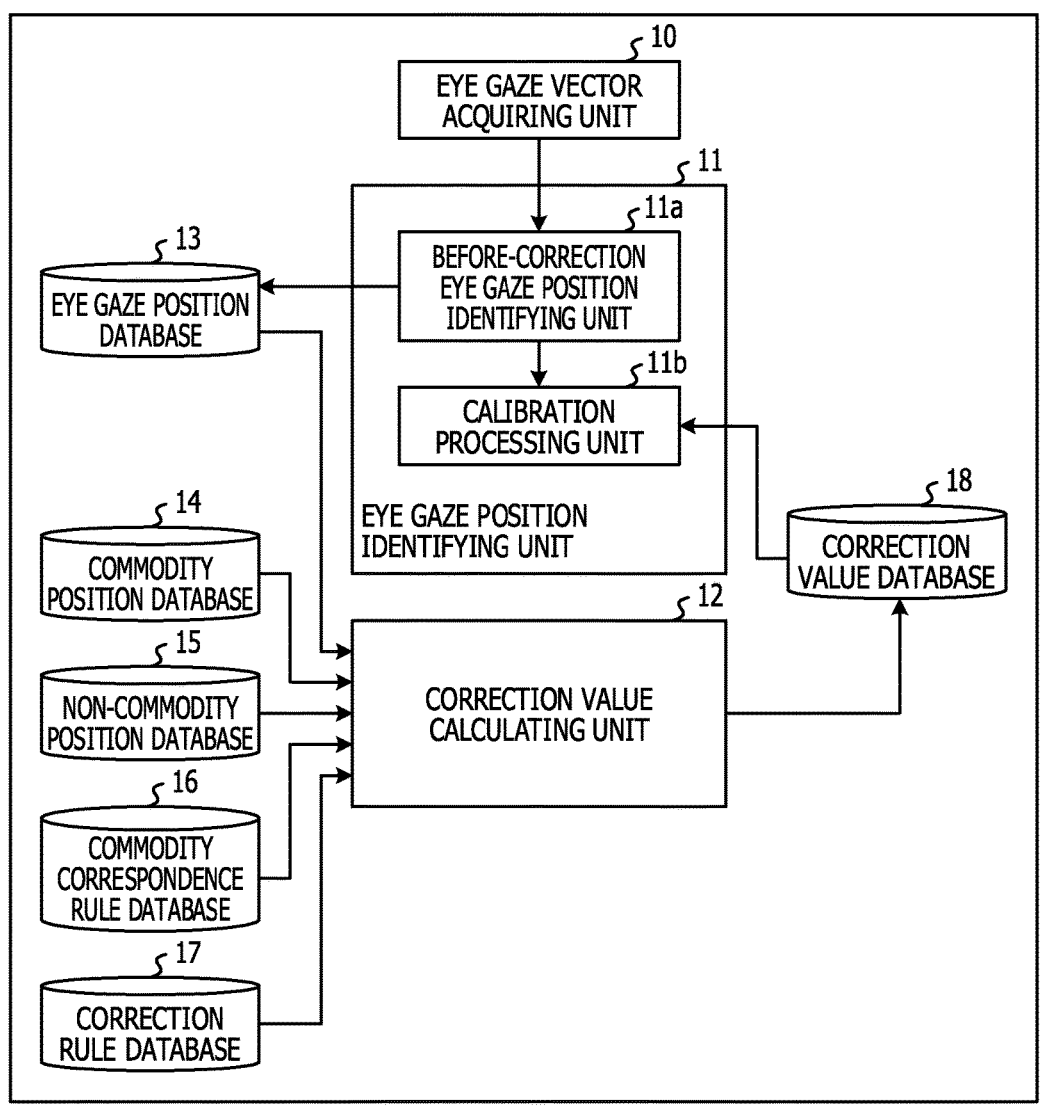
FIG. 3 is a functional block diagram of the eye gaze position detecting device 100.

FIG. 3 is a functional block diagram of the eye gaze position detecting device 100.

The eye gaze position detecting device 100 includes an eye gaze vector acquiring unit 10, an eye gaze position identifying unit 11, and a correction value calculating unit 12. The eye gaze position identifying unit 11 includes a before-correction eye gaze position identifying unit 11a and a calibration processing unit 11b. The eye gaze vector acquiring unit 10 can be implemented by the network I/F unit 106 illustrated in FIG. 2 for example. Furthermore, the eye gaze position identifying unit 11 and the correction value calculating unit 12 can be implemented by the processor 101 illustrated in FIG. 2 for example. The eye gaze position detecting device 100 further includes an eye gaze position database 13, a commodity position database (one example of object position storing unit) 14, and a non-commodity position database (one example of non-gaze object position storing unit) 15. Moreover, the eye gaze position detecting device 100 further includes a commodity correspondence rule database 16, a correction rule database 17, and a correction value database 18. The eye gaze position database 13, the commodity position database 14, the non-commodity position database 15, the commodity correspondence rule database 16, the correction rule database 17, and the correction value database 18 can be implemented by the auxiliary storage 103 illustrated in FIG. 2 for example.

The eye gaze vector acquiring unit 10 acquires the eye gaze vector of the user S from the eye gaze sensor 20. The eye gaze vector acquiring unit 10 may acquire, with the eye gaze vector, information to identify the user S relating to this eye gaze vector. The information to identify the user S relating to the eye gaze vector can be generated by the eye gaze vector calculating device 22 on the basis of a face recognition technique or the like for example.

The before-correction eye gaze position identifying unit 11a calculates the eye gaze position of the user S on the basis of the eye gaze vector acquired by the eye gaze vector acquiring unit 10. For example, the before-correction eye gaze position identifying unit 11a calculates the eye gaze position of the user S on a virtual plane M at which an object is located on the basis of the eye gaze vector and the distance between the user S and the object. The before-correction eye gaze position identifying unit 11a calculates one eye gaze position about one eye gaze vector. Therefore, the same number of eye gaze positions of the user S as the number of plural eye gaze vectors are calculated.

Here, the object is arbitrary. In the following, it is assumed that the object is a commodity as a target of a gaze by the user S as one example. Furthermore, in the following, as the commodity, an arbitrary commodity displayed in a shop is assumed as one example. Therefore, the user S is a person who comes to the shop (person who possibly purchases the commodity).

The distance between the user S and the object may be either a measured value or a fixed value (assumed value). In the following, as one example, the before-correction eye gaze position identifying unit 11a calculates the distance between the user S and the commodity (hereinafter, referred to also as the "commodity-user distance") on the basis of the pupillary distance of the user S. However, the calculation method of the commodity-user distance is arbitrary. For example, if the eye gaze sensor 20 acquires a distance image, the commodity-user distance may be calculated on the basis of the distance image.

The virtual plane M is e.g. a vertical plane including the position (coordinates) of the commodity as illustrated in FIG. 1. The eye gaze position P is the position of the point at which the eye gaze vector V1 intersects the virtual plane M as illustrated in FIG. 1. In the following, for convenience, X-, Y-, and Z-axes are defined, with the left end of the virtual plane M regarded as the origin, and it is assumed that the positive direction of the Z-axis is on the side of the user S as illustrated in FIG. 1.

The calibration processing unit 11b corrects the eye gaze position of the user S calculated by the before-correction eye gaze position identifying unit 11a on the basis of a correction value in the correction value database 18. The eye gaze position corrected by the calibration processing unit 11b is output as the final calculation result of the eye gaze position by the eye gaze position identifying unit 11.

When a correction value exists in the correction value database 18, the calibration processing unit 11b corrects the eye gaze position of the user S calculated by the before-correction eye gaze position identifying unit 11a. However, when a correction value does not exist, the calibration processing unit 11b does not carry out the correction. That a correction value does not exist includes that a correction value is 0. Hereinafter, when the eye gaze position after correction by the calibration processing unit 11b and the eye gaze position before correction by the before-correction eye gaze position identifying unit 11a are not particularly discriminated from each other, the eye gaze position will be referred to simply as the "eye gaze position calculated by the eye gaze position identifying unit 11." That is, in the following description, the "eye gaze position calculated by the eye gaze position identifying unit 11" may be either one of the eye gaze position after correction by the calibration processing unit 11b and the eye gaze position before correction by the before-correction eye gaze position identifying unit 11a.

On the basis of plural eye gaze positions calculated by the eye gaze position identifying unit 11 and position information of the commodity stored in the commodity position database 14, the correction value calculating unit 12 calculates the correction value to cause the plural eye gaze positions to match the position of the commodity indicated by the position information. Calculating the correction value may involve updating an already-existing correction value (e.g. initial value or previous value). Specific examples of the calculation method of the correction value by the correction value calculating unit 12 will be described later.

The eye gaze position database 13 stores the eye gaze positions calculated by the eye gaze position identifying unit 11. Therefore, the plural eye gaze positions calculated by the eye gaze position identifying unit 11 are stored in the eye gaze position database 13. The respective eye gaze positions in the eye gaze position database 13 may be held until being extracted by the correction value calculating unit 12. One example of the generation method of the eye gaze position database 13 will be described later with reference to FIG. 6.

Figure 5:
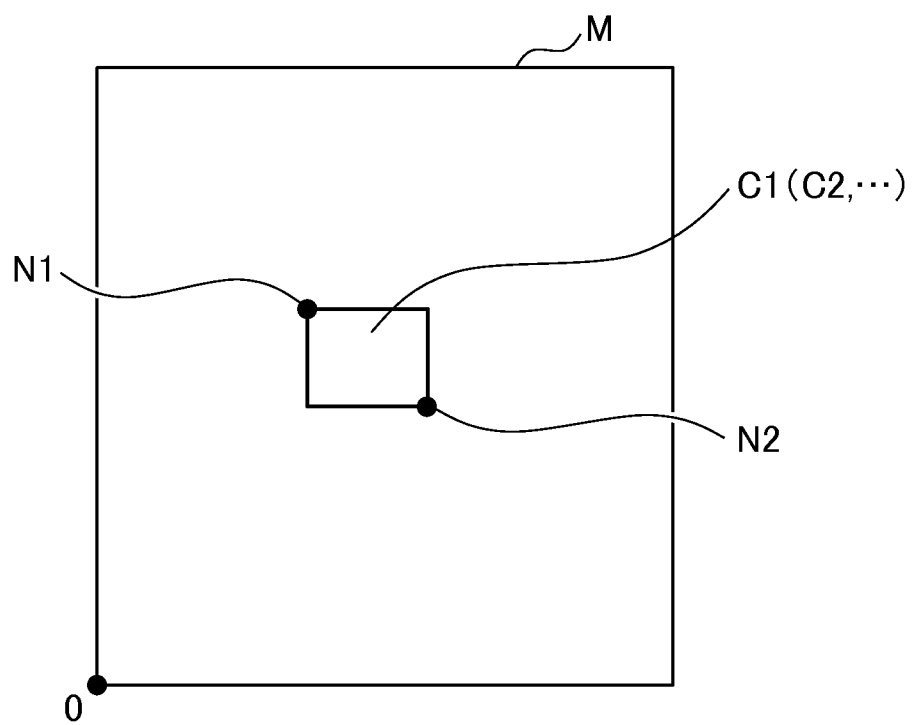
FIG. 5 is a (second) explanatory diagram of the commodity position database 14.

The commodity position database 14 stores the position information representing the positions of commodities as gaze targets of the user S. The position of the commodity represented by the position information is arbitrary and may be e.g. the center position of the commodity, the position of the centroid, the position of a part with high conspicuousness in the commodity, or the like. FIGS. 4 and 5 are explanatory diagrams of the commodity position database 14. In an example illustrated in FIG. 4, the XY-coordinates of an upper left position N1 and a lower right position N2 relating to commodities C1, C2 . . . (see FIG. 5) are stored in the commodity position database 14. The commodity position database 14 may store information relating to the shapes and sizes of commodity regions in addition to the position information of the commodities. The commodity region refers to the region occupied by a commodity on the virtual plane. However, the commodity region may be a region corresponding to a simple commodity outer shape.

The non-commodity position database 15 stores position information representing the positions of non-gaze-target objects located around the commodities (hereinafter, referred to as the "non-gaze-target object position information"). The non-gaze-target object is an object that does not become a gaze target of the user S. The object that does not become a gaze target of the user S is decided on the basis of general criteria and does not mean an object that becomes a gaze target for the peculiar user S. The non-gaze-target object is e.g. a commodity shelf itself (e.g. frame and so forth), a gap between a commodity and an adjacent commodity, a wall of a shop, a pillar, or that kind of object. The non-gaze-target object position information may be stored in association with the commodities on each commodity basis. Preferably, the non-gaze-target object position information is so generated that the positions of given objects located around the commodities are not included in the existence regions of the non-gaze-target objects indicated by the non-gaze-target object position information. The given object is an object that becomes a target of a gaze by the user S and is other than the commodity and is e.g. a tag on which explanation and price of a commodity are written or that kind of object. The position information of the given object may be stored in the commodity position database 14 in association with the commodities on each commodity basis. The non-commodity position database 15 may be omitted as appropriate.

The commodity correspondence rule database 16 stores information to identify the correspondence relationship between the eye gaze position calculated by the eye gaze position identifying unit 11 and the commodity. For example, the commodity correspondence rule database 16 stores, about each commodity, the range that can be taken by the eye gaze position calculated by the eye gaze position identifying unit 11 when the user S is gazing at the commodity. Such ranges may be calculated on the basis of the position information of the commodities in the commodity position database 14 or may be set on the basis of a test, an empirical rule, or the like. The commodity correspondence rule database 16 may be omitted as appropriate.

The correction rule database 17 stores a correction rule when correction by the correction value calculating unit 12 is carried out. The correction rule may correspond to a calculation expression (to be described later) for deriving a correction value from plural eye gaze positions calculated by the eye gaze position identifying unit 11 and the position information relating to the commodity corresponding to these plural eye gaze positions (position information in the commodity position database 14).

The correction value database 18 stores the correction value calculated by the correction value calculating unit 12. The correction value is stored on each commodity basis. Furthermore, the correction value may be stored about each of the users S, virtual planes, and user positions. Calculation methods of the correction value will be described later.

According to the eye gaze position detecting device 100 illustrated in FIG. 3, the correction value calculating unit 12 calculates the correction value on the basis of plural eye gaze positions (i.e. aggregation of eye gaze positions). Thus, the accuracy of the correction value can be enhanced compared with the case of calculating the correction value about each one eye gaze position. This is because the plural eye gaze positions do not necessarily each correspond to an eye gaze position when the user S is looking at a commodity and include, in some cases, an eye gaze position when the user S is taking a survey of the periphery of the commodity for example.

Furthermore, according to the eye gaze position detecting device 100 illustrated in FIG. 3, it is possible to calculate the correction value by using plural eye gaze positions when the user S is looking (gazing) at a commodity. This avoids the need to dispose a particular object that is other than the commodity and has high conspicuousness (reference point for calibration) for the purpose of calibration. That is, the commodity itself serves as the reference point for calibration, which avoids the need to get the user S to gaze at the reference point for calibration other than the commodity. As above, according to the eye gaze position detecting device 100 illustrated in FIG. 3, the correction value can be calculated by using plural eye gaze positions obtained in natural movement of the eye gaze of the user S (gaze at a commodity of interest or the like). This can efficiently increase the opportunities to calculate the correction value without imposing a particular burden on the user S.

Next, with reference to FIGS. 6 to 11, an operation example of the eye gaze position detecting device 100 will be described. Here, a scene (see FIG. 11) in which the camera 21 of the eye gaze sensor 20 is provided to image the user S who gazes at one certain commodity (hereinafter, referred to as the "commodity Ct") is assumed. In the example illustrated in FIG. 11, a situation in which the commodity Ct is placed on a commodity shelf 200 is schematically illustrated. In this case, the camera 21 (not illustrated) is disposed near the commodity Ct for example and has the eye gaze direction in the positive direction of the Z-axis. Furthermore, suppose that the user S (not illustrated) gazes at the commodity Ct from a position on the side of the positive direction of the Z-axis relative to the commodity Ct.

Figure 6:
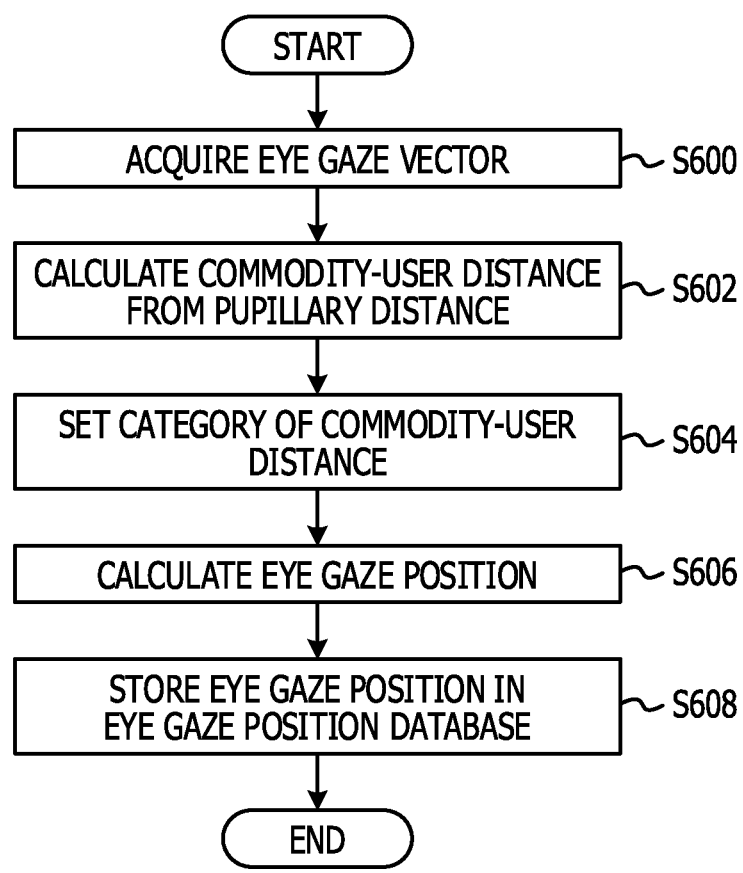
FIG. 6 is a flowchart illustrating one example of eye gaze position database generation processing executed by the eye gaze position detecting device 100.

FIG. 6 is a flowchart illustrating one example of eye gaze position database generation processing executed by the eye gaze position detecting device 100. The processing illustrated in FIG. 6 may be executed every time the eye gaze sensor 20 calculates an eye gaze vector relating to the same user S. If the eye gaze sensor 20 simultaneously calculates eye gaze vectors relating to plural users S, the processing illustrated in FIG. 6 may be executed in parallel for each of the users S.

In a step S600, the eye gaze vector acquiring unit 10 acquires the eye gaze vector of the user S from the eye gaze sensor 20. Furthermore, the eye gaze vector acquiring unit 10 acquires the pupillary distance of the user S from the eye gaze sensor 20. For example, the eye gaze sensor 20 transmits, to the eye gaze position detecting device 100, the pupillary distance of the user S obtained from an image used when the eye gaze vector is calculated in association with the eye gaze vector.

In a step S602, the before-correction eye gaze position identifying unit 11a calculates the commodity-user distance on the basis of the pupillary distance of the user S. For example, the before-correction eye gaze position identifying unit 11a may calculate the commodity-user distance with reference to information indicating the relationship between the pupillary distance and the commodity-user distance like information illustrated in FIG. 7. The calculation of the commodity-user distance may be implemented by the eye gaze sensor 20. In this case, the eye gaze vector acquiring unit 10 may acquire the commodity-user distance from the eye gaze sensor 20 instead of the pupillary distance. In this case, the processing of the step S602 is omitted.

In a step S604, the before-correction eye gaze position identifying unit 11a sets the category of the commodity-user distance calculated in the step S602. For example, the before-correction eye gaze position identifying unit 11a may set the category of the commodity-user distance with reference to information indicating the relationship between the commodity-user distance and the category like information illustrated in FIG. 8. Here, the category is set in view of the point that the calculated commodity-user distance does not have high accuracy. However, it is also possible to use the calculated commodity-user distance directly. In this case, the processing of the step S604 is omitted.

In a step S606, the before-correction eye gaze position identifying unit 11a calculates an eye gaze position corresponding to the eye gaze vector acquired in the step S600. At this time, the before-correction eye gaze position identifying unit 11a sets (estimates) the Z-coordinate of the starting point of the eye gaze vector of the user S on the basis of the category set in the step S604. That is, the before-correction eye gaze position identifying unit 11a sets the distance between the virtual plane M and the starting point of the eye gaze vector of the user S (distance in the Z-direction). For example, in the case of a category "T1" represented in FIG. 8, the before-correction eye gaze position identifying unit 11a sets the Z-coordinate of the starting point of the eye gaze vector of the user S to e.g. 50 [cm]. Furthermore, in the case of a category "T2" represented in FIG. 8, the before-correction eye gaze position identifying unit 11a sets the Z-coordinate of the starting point of the eye gaze vector of the user S to e.g. 75 [cm]. Moreover, in the case of a category "T3" represented in FIG. 8, the before-correction eye gaze position identifying unit 11a sets the Z-coordinate of the starting point of the eye gaze vector of the user S to e.g. 100 [cm]. Such distance in the Z-direction according to the category may be set in advance on the basis of the width of an aisle in front of the commodity Ct and so forth. Furthermore, it is also possible to set the Z-coordinate of the starting point of the eye gaze vector of the user S by using the commodity-user distance directly. In this case, the before-correction eye gaze position identifying unit 11a sets the Z-coordinate of the starting point of the eye gaze vector of the user S to the value of the commodity-user distance. On the basis of the set Z-coordinate of the starting point of the eye gaze vector, the before-correction eye gaze position identifying unit 11a calculates the intersection at which the eye gaze vector intersects the virtual plane M (see the eye gaze position P in FIG. 1) as the eye gaze position.

In a step S608, the before-correction eye gaze position identifying unit 11a stores the eye gaze position calculated in the step S606 in the eye gaze position database 13. Alternatively, if a correction value exists in the correction value database 18, the calibration processing unit 11b may correct the eye gaze position calculated by the before-correction eye gaze position identifying unit 11a in the step S606 by the correction value and then store the corrected eye gaze position in the eye gaze position database 13. In this manner, plural eye gaze positions calculated by the eye gaze position identifying unit 11 are stored (accumulated) in the eye gaze position database 13. At this time, the plural eye gaze positions may be stored about each of the users S, the virtual planes, and the commodity-user distances. In the following, it is assumed that the plural eye gaze positions are stored about each user S.

Figure 9:
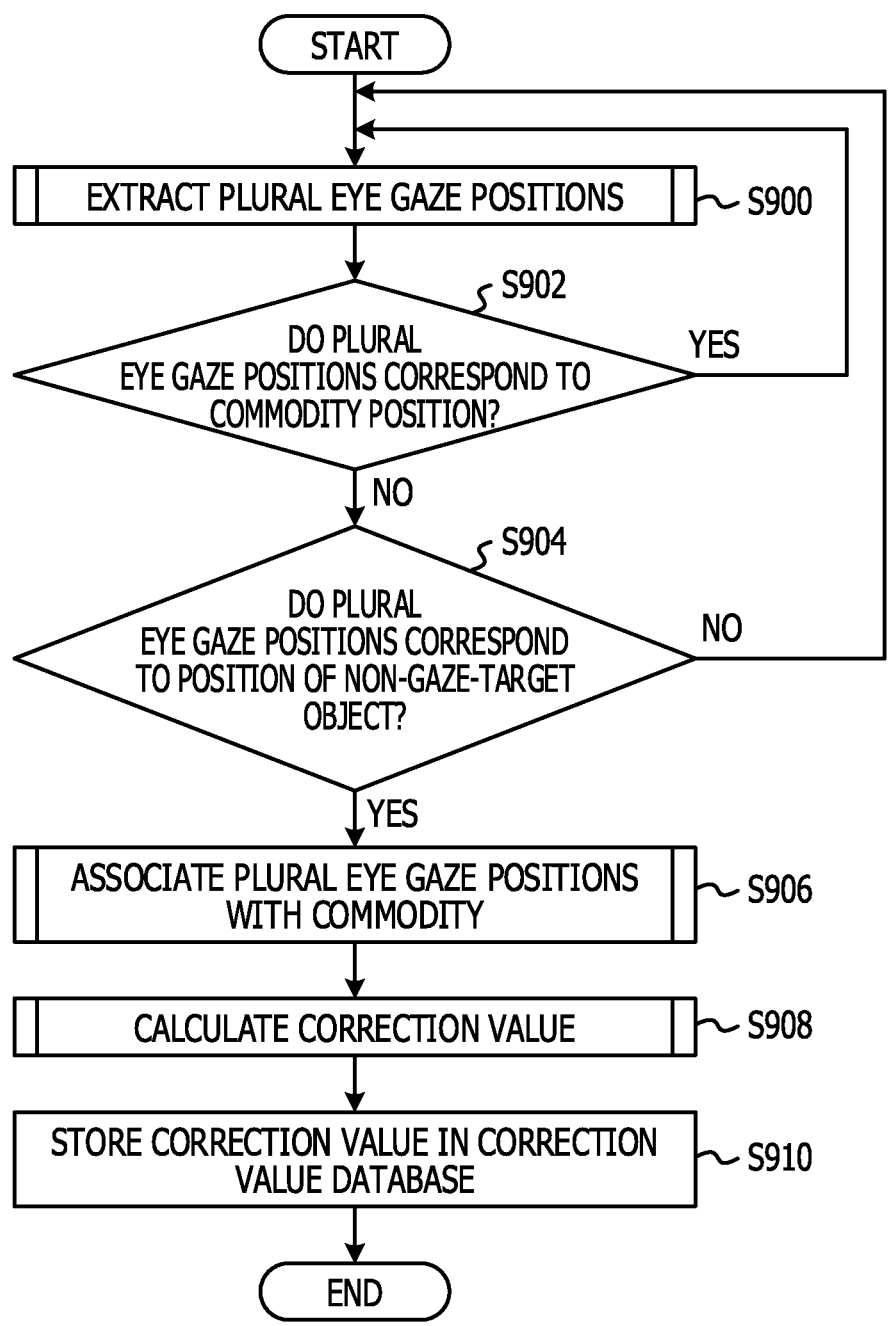
FIG. 9 is a flowchart illustrating one example of correction value database generation processing executed by the eye gaze position detecting device 100.

FIG. 9 is a flowchart illustrating one example of correction value database generation processing executed by the eye gaze position detecting device 100. The processing illustrated in FIG. 9 may be executed every time a given number of eye gaze positions calculated by the eye gaze position identifying unit 11 are accumulated in the eye gaze position database 13 or may be executed every given time for example.

In a step S900, the correction value calculating unit 12 extracts plural eye gaze positions (one example of first plural eye gaze positions) from the eye gaze position database 13. Preferably, the extracted plural eye gaze positions are eye gaze positions relating to the same user S. In this case, the extracted plural eye gaze positions may be all eye gaze positions relating to the same user S. Alternatively, the extracted plural eye gaze positions may be eye gaze positions that are obtained per given time and relate to the same user S. The number of extracted eye gaze positions depends on the time for which the user S looks at a commodity, the frame rate of the camera 21, and so forth. Alternatively, the correction value calculating unit 12 may extract only plural eye gaze positions satisfying a given condition (another example of the first plural eye gaze positions) among plural eye gaze positions relating to the same user S (one example of second plural eye gaze positions) in the eye gaze position database 13. The plural eye gaze positions satisfying the given condition may be e.g. plural eye gaze positions forming an aggregation whose spread is small (distances from adjacent eye gaze positions are short). Furthermore, the plural eye gaze positions satisfying the given condition may be plural eye gaze positions existing near a commodity (for example in a range set on the basis of the commodity-user distance and a detection error). An example of this kind of extraction processing (eye gaze position selection processing) will be described later with reference to FIG. 19 and so forth.

In a step S902, the correction value calculating unit 12 refers to position information relating to the commodity Ct in the commodity position database 14 and determines whether or not the plural eye gaze positions extracted in the step S900 correspond to the position of the commodity Ct. Whether or not the plural eye gaze positions correspond to the position of the commodity Ct may be determined by an arbitrary method. For example, the correction value calculating unit 12 may determine that the plural eye gaze positions correspond to the position of the commodity Ct if the position of the centroid (average position) of the plural eye gaze positions exists in a rectangular region (commodity region) defined by the upper left position N1 and the lower right position N2 relating to the commodity Ct. The position of the centroid of the plural eye gaze positions may correspond to the position of the centroid obtained when the same mass is given to each eye gaze position. If the plural eye gaze positions correspond to the position of the commodity Ct, the correction value calculating unit 12 determines that calculation of a correction value is unnecessary and the processing returns to the step S900. In the other case, the processing proceeds to a step S904.

In the step S904, the correction value calculating unit 12 refers to non-gaze-target object position information associated with the commodity Ct in the non-commodity position database 15 and determines whether or not the plural eye gaze positions extracted in the step S900 correspond to the position of a non-gaze-target object. Whether or not the plural eye gaze positions correspond to the position of a non-gaze-target object may be determined by an arbitrary method and may be determined by a method similar to that of the step S902. That is, the correction value calculating unit 12 may determine that the plural eye gaze positions correspond to the position of a non-gaze-target object if the position of the centroid of the plural eye gaze positions exists in the existence region of the non-gaze-target object indicated by the non-gaze-target object position information. If the plural eye gaze positions correspond to the position of a non-gaze-target object, the processing proceeds to a step S906. In the other case, the correction value calculating unit 12 determines that calculation of a correction value is unnecessary and the processing returns to the step S900. The case in which the negative determination is made in the step S904 is e.g. a case in which the position of the centroid of the plural eye gaze positions exists in the existence region of the given object (e.g. price tag), or the like.

In the step S906, the correction value calculating unit 12 refers to the commodity correspondence rule database 16 and associates the plural eye gaze positions extracted in the step S900 with a commodity in the commodity position database 14. For example, the correction value calculating unit 12 associates a commodity having the position information closest to the plural eye gaze positions extracted in the step S900 with the plural eye gaze positions extracted in the step S900. In the present example, the correction value calculating unit 12 associates the plural eye gaze positions extracted in the step S900 with the commodity Ct in the commodity position database 14. If this associating cannot be carried out, the processing may return to the step S900. As the case in which the associating cannot be carried out, for example there is a case in which there is a possibility that the plural eye gaze positions extracted in the step S900 are eye gaze positions when the user S is gazing at e.g. another commodity other than the commodity Ct (another commodity as a target of a gaze by the user S).

In a step S908, the correction value calculating unit 12 calculates a correction value to cause the plural eye gaze positions extracted in the step S900 to match the position of the commodity Ct based on the position information in the commodity position database 14. The calculation method of the correction value is arbitrary. Examples of the calculation method of the correction value will be described later.

In a step S910, the correction value calculating unit 12 stores the correction value calculated in the step S908 in the correction value database 18. The correction value calculating unit 12 may store the correction value relating to the commodity Ct about each user S or may store one correction value relating to the commodity Ct irrespective of who the user S is. Furthermore, if the correction value relating to the commodity Ct has been already stored in the correction value database 18, the correction value calculating unit 12 updates the correction value. The updating of the correction value may be overwriting or may involve averaging with the already-existing correction value.

According to the processing illustrated in FIG. 9, the correction value is calculated on the basis of plural eye gaze positions (i.e. aggregation of eye gaze positions). Thus, the accuracy of the correction value can be enhanced compared with the case of calculating the correction value about each one eye gaze position. This is because the plural eye gaze positions do not necessarily each correspond to an eye gaze position when the user S is looking at the commodity Ct and include, in some cases, an eye gaze position when the user S is taking a survey of the periphery of the commodity Ct for example.

Furthermore, according to the processing illustrated in FIG. 9, as described above, if plural eye gaze positions correspond to the position of a non-gaze-target object (YES of the step S904), the correction value calculating unit 12 calculates a correction value to cause the plural eye gaze positions corresponding to the position of the non-gaze-target object to match the position of the commodity Ct. This can enhance the accuracy of the correction value. This is because the plural eye gaze positions corresponding to the position of a non-gaze-target object have a high likelihood of being plural eye gaze positions when the user S is looking (gazing) at the commodity Ct. For example, it is unnatural for the user S to gaze at a non-gaze-target object such as a commodity shelf itself. Therefore, the plural eye gaze positions corresponding to the position of a non-gaze-target object tend to have a high likelihood of being plural eye gaze positions when the user S is looking (gazing) at the commodity Ct around the non-gaze-target object. That is, the possibility that the plural eye gaze positions do not correspond to the position of the commodity Ct due to an error in the calculation of the eye gaze positions is high. Therefore, the accuracy of the correction value can be enhanced by calculating the correction value to cause the plural eye gaze positions to match the position of the commodity Ct on the basis of the plural eye gaze positions corresponding to the position of the non-gaze-target object.

Moreover, according to the processing illustrated in FIG. 9, it becomes possible to calculate the correction value by using plural eye gaze positions when the user S is looking (gazing) at the commodity Ct. This avoids the need to separately dispose a reference point for calibration. As above, according to the processing illustrated in FIG. 9, the correction value can be calculated by using plural eye gaze positions obtained in natural movement of the eye gaze of the user S (gaze at the commodity Ct of interest or the like). This can efficiently increase the opportunities to calculate the correction value without imposing a particular burden on the user S.

In the example illustrated in FIG. 9, the processing of the step S902 and/or the step S904 may be omitted. For example, the processing of the step S904 may be omitted if the non-gaze-target object is not assumed. In this case, the non-commodity position database 15 may also be omitted.

Figure 10:
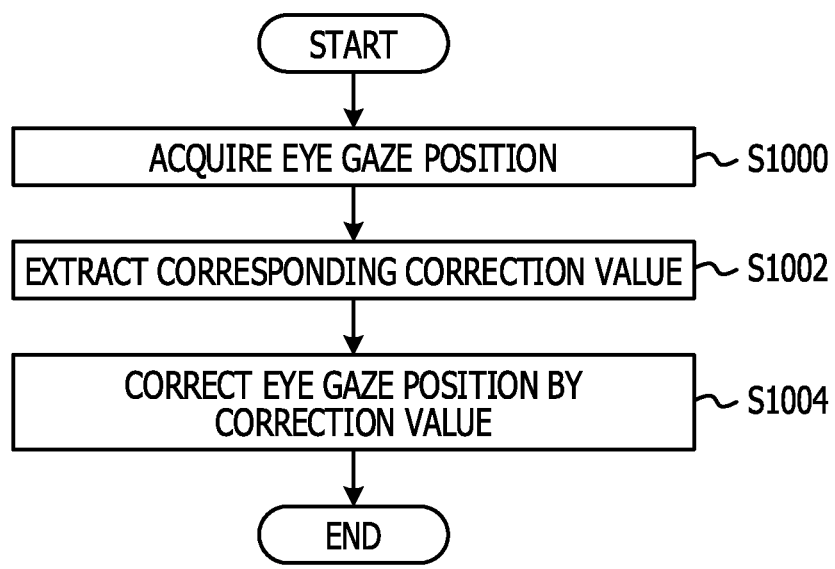
FIG. 10 is a flowchart illustrating one example of calibration processing executed by the eye gaze position detecting device 100.

FIG. 10 is a flowchart illustrating one example of calibration processing executed by the eye gaze position detecting device 100. The processing illustrated in FIG. 10 is executed every time the before-correction eye gaze position identifying unit 11a calculates an eye gaze position.

In a step S1000, the calibration processing unit 11b acquires an eye gaze position calculated in the before-correction eye gaze position identifying unit 11a.

In a step S1002, the calibration processing unit 11b extracts a correction value corresponding to the eye gaze position acquired in the step S1000 from the correction value database 18. For example, if the correction value relating to the commodity Ct is stored in the correction value database 18 on each user basis, the calibration processing unit 11b extracts the correction value relating to the present user S. If only one correction value is stored as the correction value relating to the commodity Ct in the correction value database 18, the calibration processing unit 11b extracts the correction value relating to the commodity Ct.

In a step S1004, the calibration processing unit 11b corrects the eye gaze position acquired in the step S1000 on the basis of the correction value extracted in the step S1002. The correction method is arbitrary. Examples of the correction method will be described later in relation to calculation methods of the correction value. The calibration processing unit 11b may store the corrected eye gaze position in the eye gaze position database 13.

According to the processing illustrated in FIG. 10, calibration can be carried out by using the correction value with high accuracy as described above. This can output the eye gaze position with high accuracy.

The processing illustrated in FIG. 10 is executed every time the before-correction eye gaze position identifying unit 11a calculates an eye gaze position. However, another mode may be employed. For example, the processing illustrated in FIG. 10 may be collectively executed on plural eye gaze positions that are stored in the eye gaze position database 13 and are calculated by the before-correction eye gaze position identifying unit 11a.

Next, examples of the calculation method of the correction value (correction rule) will be described with reference to FIGS. 11 to 17. Also here, a scene (see FIG. 11) in which the camera 21 of the eye gaze sensor 20 is provided to image the user S who gazes at one certain commodity Ct is assumed.

Figure 12:
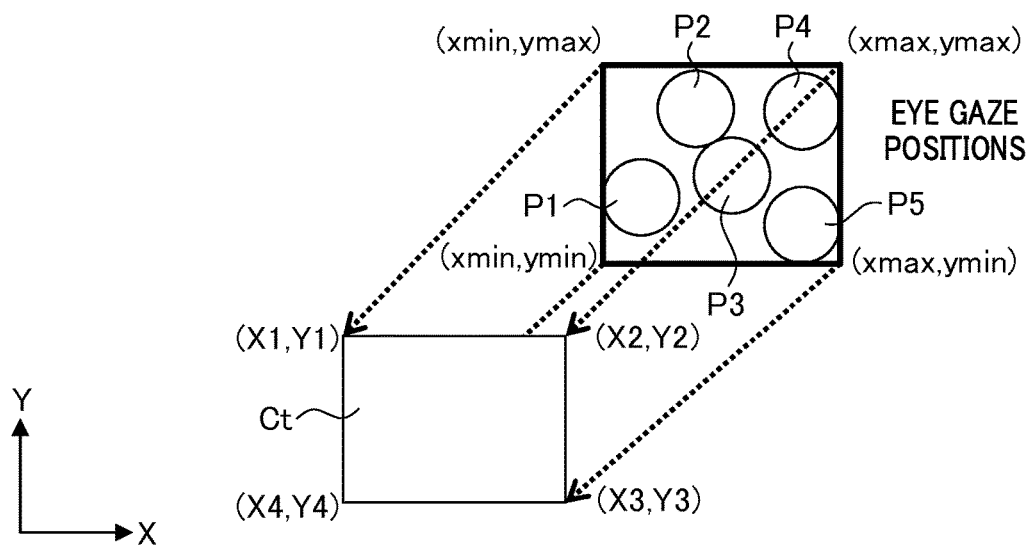
FIG. 12 is an explanatory diagram of one example of a correction rule.

FIG. 12 is an explanatory diagram of one example of the correction rule. In FIG. 12, plural eye gaze positions P1 to P5 and the commodity Ct on the virtual plane M are schematically illustrated. In the example of the correction rule illustrated in FIG. 12, the correction value is represented by the following transformation matrix.

$$\begin{pmatrix} a & b & c \\ d & e & f \\ 0 & 0 & 1 \end{pmatrix} \quad \text{[Expression 1]}$$

Figure 13:
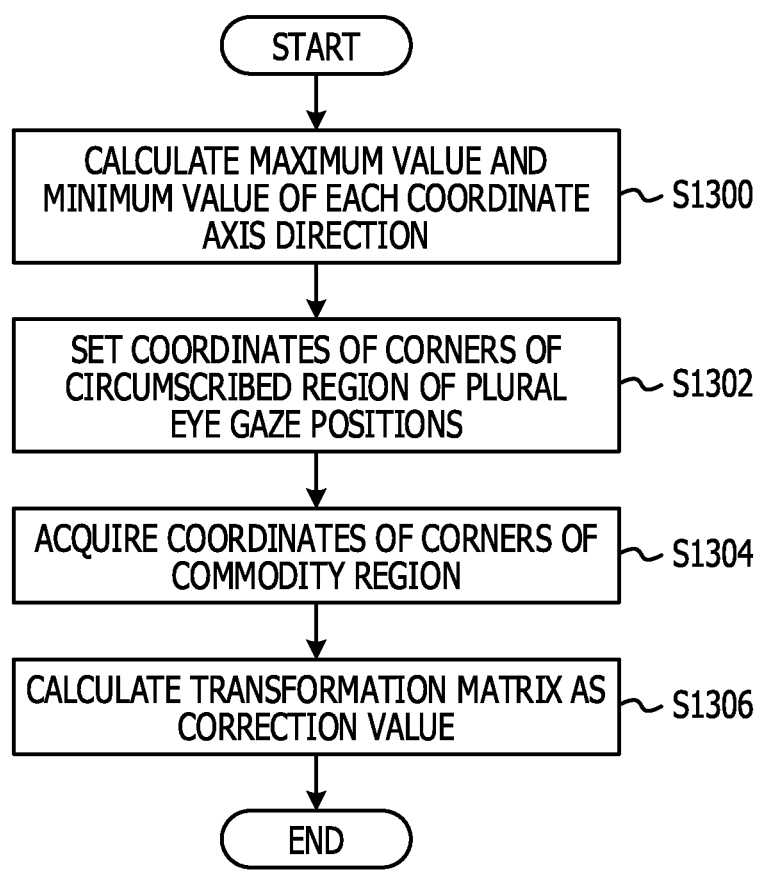
FIG. 13 is a flowchart illustrating correction value calculation processing based on one example of the correction rule.

FIG. 13 is a flowchart illustrating correction value calculation processing based on one example of the correction rule. The processing illustrated in FIG. 13 is executed as one example of the processing of the step S908 illustrated in FIG. 9.

In a step S1300, the correction value calculating unit 12 calculates the maximum value (xmax) and the minimum value (xmin) of the X-coordinate of the plural eye gaze positions extracted in the step S900 and the maximum value (ymax) and the minimum value (ymin) of the Y-coordinate thereof. In FIG. 12, the maximum value (xmax) and the minimum value (xmin) of the X-coordinate of the plural eye gaze positions P1 to P5 and the maximum value (ymax) and the minimum value (ymin) of the Y-coordinate thereof are diagrammatically represented.

In a step S1302, the correction value calculating unit 12 sets the coordinates of each corner of a circumscribed region that is circumscribed to the plural eye gaze positions extracted in the step S900 on the basis of the respective values calculated in the step S1300. As illustrated in FIG. 12, the coordinates of the respective corners are set as follows: (xmin, ymax) for the upper left corner; (xmax, ymax) for the upper right corner; (xmax, ymin) for the lower right corner; and (xmin, ymin) for the lower left corner.

In a step S1304, the correction value calculating unit 12 refers to the commodity position database 14 and acquires the coordinates of each corner of the commodity region relating to the commodity Ct. In the example illustrated in FIG. 12, the coordinates of the respective corners of the commodity region relating to the commodity Ct are as follows: (X1, Y1) for the upper left corner; (X2, Y2) for the upper right corner; (X3, Y3) for the lower right corner; and (X4, Y4) for the lower left corner.

In a step S1306, the correction value calculating unit 12 calculates the respective values a, b, c, d, e, and f in the transformation matrix represented in Expression 1 so that the coordinates of the respective corners set in the steps S1302 and S1304 may correspond. That is, the correction value calculating unit 12 obtains the respective values a to f of the transformation matrix with which (xmin, ymax), (xmax, ymax), (xmax, ymin), and (xmin, ymin) become (X1, Y1), (X2, Y2), (X3, Y3), and (X4, Y4), respectively. The correction value calculating unit 12 stores the calculated respective values a, b, c, d, e, and f in the correction value database 18 as a correction value (see the step S910 in FIG. 9).

With the correction rule illustrated in FIGS. 12 and 13, the calibration processing unit 11b may correct an eye gaze position calculated by the before-correction eye gaze position identifying unit 11a in accordance with the following expression.

$$\begin{pmatrix} u \\ v \\ 1 \end{pmatrix} = \begin{pmatrix} a & b & c \\ d & e & f \\ 0 & 0 & 1 \end{pmatrix} \begin{pmatrix} x \\ y \\ 1 \end{pmatrix} \quad \text{[Expression 2]}$$

Here, (x, y) represents the X-coordinate and the Y-coordinate of the eye gaze position calculated by the before-correction eye gaze position identifying unit 11a, and (u, v) represents the X-coordinate and the Y-coordinate of the eye gaze position after the correction by the calibration processing unit 11b.

According to the correction rule illustrated in FIGS. 12 and 13, eye gaze positions in the rectangular region circumscribed to the plural eye gaze positions extracted in the step S900 can be corrected into the commodity region relating to the commodity Ct. Although affine transformation is presented as the transformation matrix as an example in the correction rule illustrated in FIGS. 12 and 13, projective transformation or the like may be used besides the affine transformation. Furthermore, the correction value may be expressed by not a matrix but a function. In addition, the shape of the circumscribed region may be an arbitrary shape such as a shape based on the shape of a commodity region, besides a rectangular shape.

Figure 14:
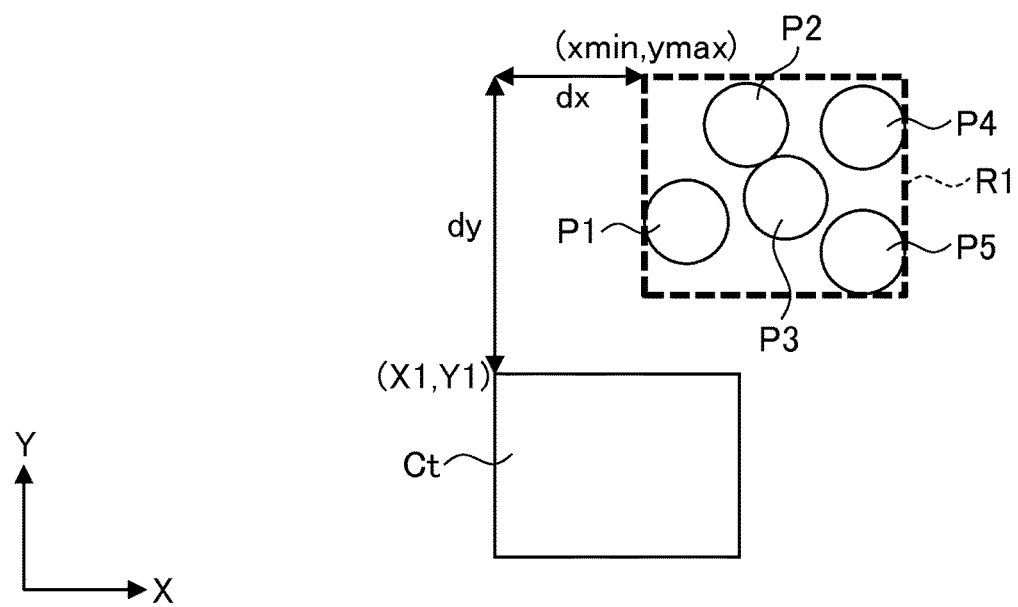
FIG. 14 is an explanatory diagram of another example of the correction rule.
Figure 15:
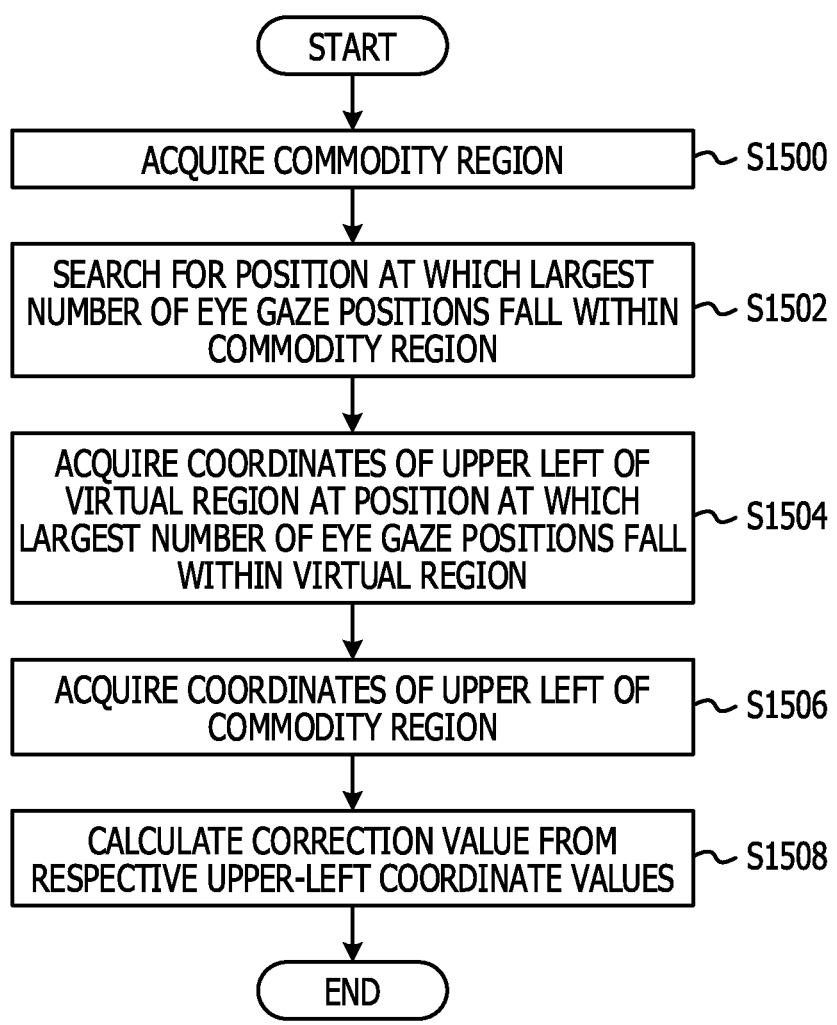
FIG. 15 is a flowchart illustrating correction value calculation processing based on another example of the correction rule.

FIG. 14 is an explanatory diagram of another example of the correction rule. In FIG. 14, plural eye gaze positions P1 to P5 and the commodity Ct on the virtual plane M are schematically illustrated. FIG. 15 is a flowchart illustrating correction value calculation processing based on another example of the correction rule. The processing illustrated in FIG. 15 is executed as one example of the processing of the step S908 illustrated in FIG. 9.

In a step S1500, the correction value calculating unit 12 refers to the commodity position database 14 and acquires the shape and size of the commodity region relating to the commodity Ct. The shape and size of the commodity region relating to the commodity Ct may be calculated on the basis of the coordinates of each corner of the commodity region relating to the commodity Ct.

In a step S1502, the correction value calculating unit 12 searches for the position of the commodity region at which the largest number of plural eye gaze positions extracted in the step S900 fall within the commodity region while virtually moving the commodity region relating to the commodity Ct on the virtual plane M. That is, the correction value calculating unit 12 disposes a region R1 having the same size and shape as the commodity region relating to the commodity Ct (hereinafter, referred to as the "virtual region R1") at the position at which the maximum number of eye gaze positions among the plural eye gaze positions extracted in the step S900 fall within the virtual region R1. If there are plural positions of the virtual region R1 at which the largest number of eye gaze positions fall within the virtual region R1, the correction value calculating unit 12 selects the position of the virtual region R1 at which the distance between given reference positions (to be described later) is the shortest. Alternatively, the correction value calculating unit 12 may decide the position of the virtual region R1 in such a manner as to minimize the sum of the distances between the centroid of the region having the same size and shape as the commodity region relating to the commodity Ct and a respective one of the plural eye gaze positions extracted in the step S900.

In a step S1504, the correction value calculating unit 12 acquires the coordinates of the given reference position of the virtual region R1 at the position decided in the step S1502. The given reference position is arbitrary in the virtual region R1. In the example illustrated in FIG. 14, the given reference position is the upper left corner and the XY-coordinates thereof are (xmin, ymax).

In a step S1506, the correction value calculating unit 12 refers to the commodity position database 14 and acquires the coordinates of the corresponding given reference position of the commodity region relating to the commodity Ct. The corresponding given reference position means a position corresponding to the given reference position of the virtual region R1 and is determined depending on the given reference position of the virtual region R1. In the example illustrated in FIG. 14, corresponding to that the given reference position of the virtual region R1 is the upper left corner of the virtual region R1, the corresponding given reference position of the commodity region is the upper left corner of the commodity region and the XY-coordinates thereof are (X1, Y1).

In a step S1508, the correction value calculating unit 12 calculates a correction value (dx, dy) so that the XY-coordinates of the respective given reference positions obtained in the steps S1504 and S1506 may correspond. That is, the correction value (dx, dy) corresponds to the amount of offset of the respective given reference positions obtained in the steps S1504 and S1506. For example, the correction value calculating unit 12 calculates the correction value (dx, dy) by defining dx=xmin−X1 and dy=ymax−Y1. The correction value calculating unit 12 stores the calculated correction value (dx, dy) in the correction value database 18 (see the step S910 in FIG. 9).

With the correction rule illustrated in FIGS. 14 and 15, the calibration processing unit 11b may correct an eye gaze position calculated by the before-correction eye gaze position identifying unit 11a in accordance with the following expression.

$$\begin{pmatrix} u \\ v \end{pmatrix} = \begin{pmatrix} x \\ y \end{pmatrix} - \begin{pmatrix} dx \\ dy \end{pmatrix}$$ [Expression 3]

Here, (x, y) represents the X-coordinate and the Y-coordinate of the eye gaze position calculated by the before-correction eye gaze position identifying unit 11a, and (u, v) represents the X-coordinate and the Y-coordinate of the eye gaze position after the correction by the calibration processing unit 11b.

Figure 16:
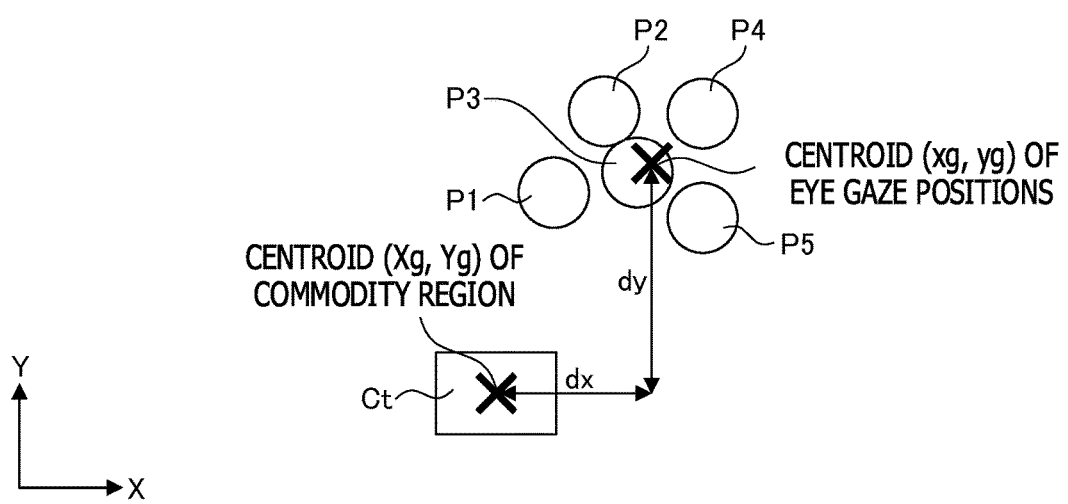
FIG. 16 is an explanatory diagram of further another example of the correction rule.
Figure 17:
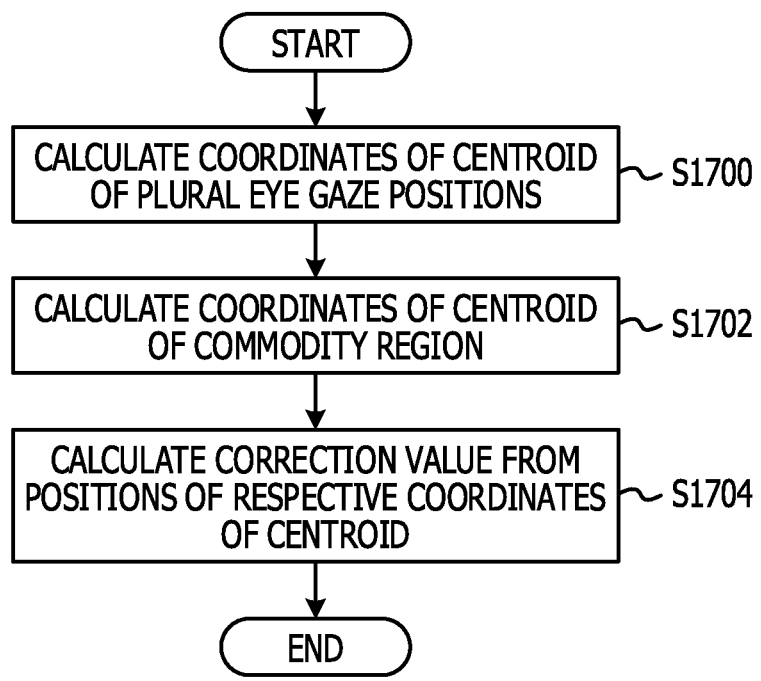
FIG. 17 is a flowchart illustrating correction value calculation processing based on further another example of the correction rule.

FIG. 16 is an explanatory diagram of further another example of the correction rule. In FIG. 16, plural eye gaze positions P1 to P5 and the commodity Ct on the virtual plane M are schematically illustrated. FIG. 17 is a flowchart illustrating correction value calculation processing based on further another example of the correction rule. The processing illustrated in FIG. 17 is executed as one example of the processing of the step S908 illustrated in FIG. 9.

In a step S1700, the correction value calculating unit 12 calculates the XY-coordinates of the position of the centroid of the plural eye gaze positions extracted in the step S900. In the example illustrated in FIG. 16, the XY-coordinates (xg, yg) of the position of the centroid of the plural eye gaze positions P1 to P5 are calculated. Furthermore, besides the position of the centroid, another position such as the eye gaze position closest to the centroid or the most frequent eye gaze position may be employed.

In a step S1702, the correction value calculating unit 12 refers to the commodity position database 14 and calculates the XY-coordinates (Xg, Yg) of a given position (in the present example, the position of the centroid) of the commodity region relating to the commodity Ct. The given position may be another position such as the position of a part with high conspicuousness in the commodity Ct instead of the position of the centroid of the commodity region.

In a step S1704, the correction value calculating unit 12 calculates a correction value (dx, dy) so that the XY-coordinates of the respective positions of the centroid obtained in the steps S1700 and S1702 may correspond. That is, the correction value (dx, dy) corresponds to the amount of offset of the respective positions of the centroid obtained in the steps S1700 and S1702. For example, the correction value calculating unit 12 calculates the correction value (dx, dy) by defining dx=xg−Xg and dy=yg−Yg. The correction value calculating unit 12 stores the calculated correction value (dx, dy) in the correction value database 18 (see the step S910 in FIG. 9).

With the correction rule illustrated in FIGS. 16 and 17, the calibration processing unit 11b may correct an eye gaze position calculated by the before-correction eye gaze position identifying unit 11a in accordance with the expression represented in Expression 3.

According to the correction rules illustrated in FIGS. 11 to 17, the correction value is calculated by using plural eye gaze positions. Therefore, the accuracy of the correction value can be enhanced compared with the case of calculating the correction value about each one eye gaze position.

Next, with reference to FIGS. 18 to 20, extraction processing for extraction (selection) of only plural eye gaze positions satisfying a given condition by the correction value calculating unit 12 (hereinafter, referred to as the "eye gaze position selection processing") will be described.

Figure 11:
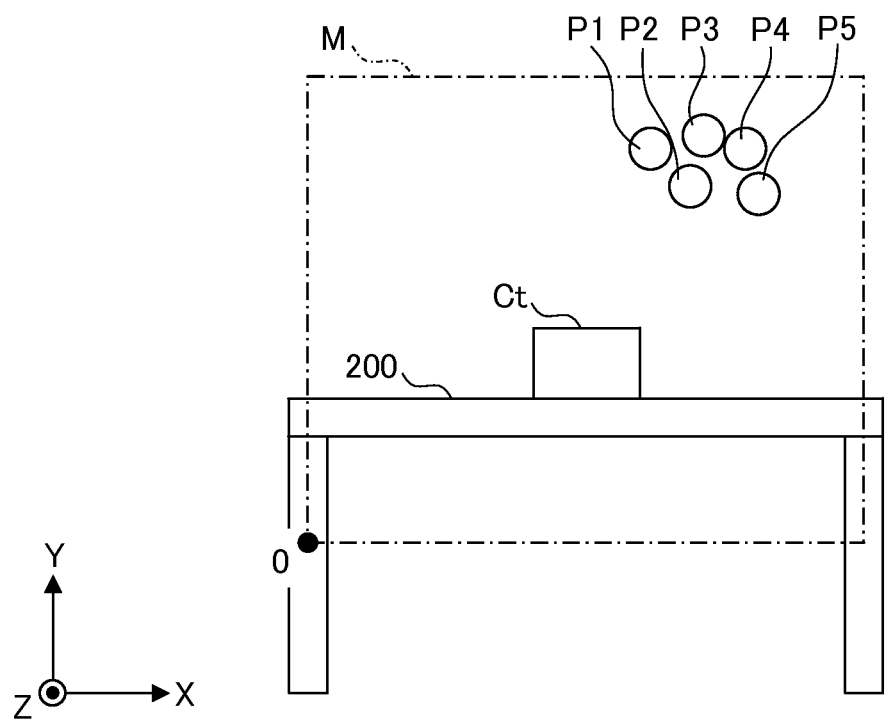
FIG. 11 is a diagram illustrating one example of an assumed scene.
Figure 18:
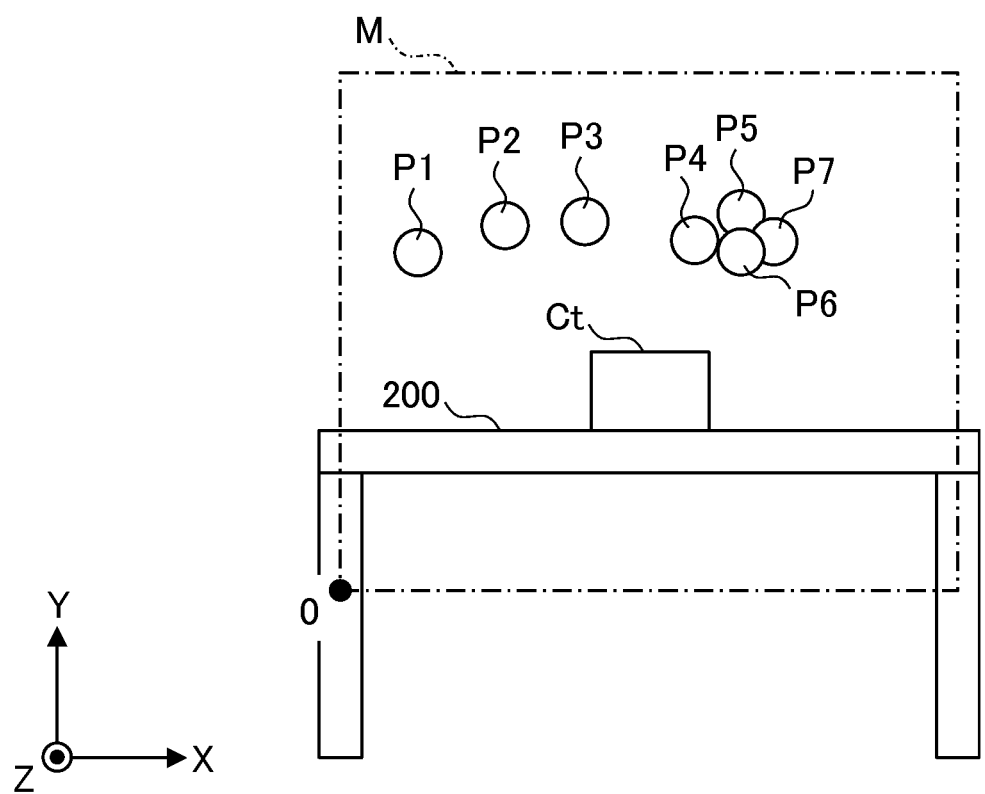
FIG. 18 is an explanatory diagram of eye gaze position selection processing.

FIG. 18 is a diagram illustrating the same scene as the scene illustrated in FIG. 11. In FIG. 18, plural eye gaze positions P1 to P7 and the commodity Ct on the virtual plane M are schematically illustrated.

FIG. 19 is a flowchart illustrating one example of the eye gaze position selection processing executed by the correction value calculating unit 12. The processing illustrated in FIG. 19 is executed as one example of the processing of the step S900 illustrated in FIG. 9.

In a step S1900, the correction value calculating unit 12 extracts all eye gaze positions relating to the same user S (one example of the second plural eye gaze positions) from the eye gaze position database 13 as initial extraction.

In a step S1902, the correction value calculating unit 12 carries out clustering of all eye gaze positions extracted in the step S1900 as the initial extraction on the basis of the respective positions. The clustering method is arbitrary. For example, the clustering method may be a hierarchical clustering method or may be a non-hierarchical clustering method. As the hierarchical clustering, there are the nearest neighbor method (single linkage method), the farthest neighbor method (complete linkage method), and so forth. Furthermore, as the non-hierarchical clustering, the k-means method may be used.

In a step S1904, about plural clusters obtained by the clustering in the step S1902, the correction value calculating unit 12 counts the number of eye gaze positions in each cluster, i.e. the numbers of eye gaze positions forming the respective clusters.

In a step S1906, the correction value calculating unit 12 selects the cluster in which the number of included eye gaze positions is the largest on the basis of the count result in the step S1904.

In a step S1908, the correction value calculating unit 12 determines whether or not the number of eye gaze positions in the cluster selected in the step S1906 is equal to or larger than a given threshold. Here, the given threshold is 50% of the number of all eye gaze positions. However, 50% is one example and another numerical value may be used. If the number of eye gaze positions in the cluster selected in the step S1906 is equal to or larger than 50% of the number of all eye gaze positions, the processing proceeds to a step S1912. In the other case, the processing proceeds to a step S1910.

In the step S1910, the correction value calculating unit 12 refers to the commodity position database 14 and selects the cluster closest to the position of the commodity Ct among the plural clusters obtained in the clustering in the step S1902. That is, the correction value calculating unit 12 reselects the cluster closest to the position of the commodity Ct as substitute for the currently-selected cluster, in which the number of eye gaze positions is the largest. The distances between the commodity Ct and a respective one of the clusters may be calculated on the basis of the positions of the centroid of the eye gaze positions forming the respective clusters.

In the step S1912, the correction value calculating unit 12 extracts all eye gaze positions in the currently-selected cluster (another example of the first plural eye gaze positions). The currently-selected cluster is the cluster in which the number of eye gaze positions is the largest (cluster selected in the step S1906) when the determination result of the step S1908 is the positive determination. Furthermore, the currently-selected cluster is the cluster closest to the position of the commodity Ct (cluster reselected in the step S1910) when the determination result of the step S1908 is the negative determination. All eye gaze positions extracted in the step S1912 in this manner are used in the processing of the step S902 and the subsequent steps in FIG. 9 as the "plural eye gaze positions extracted in the step S900 (another example of the first plural eye gaze positions)."

Incidentally, there are a variety of ways in which the user S gazes at the commodity Ct. That is, the user S immediately turns user's gaze to the commodity Ct in some cases, and the user S gazes at the commodity Ct after taking a survey of the periphery in other cases. For example, in the example illustrated in FIG. 18, the eye gaze positions P1 to P3 each exist at an isolated position, whereas the eye gaze positions P4 to P7 exist at positions comparatively close to each other. In such a situation, the eye gaze positions P1 to P3 have a low likelihood of being eye gaze positions when the user S is gazing at the commodity Ct. This is because there is a tendency that plural eye gaze positions are comparatively close to each other when the user S is gazing at the commodity Ct. For example, generally when a person gazes at an object, the person tends to keep on looking at (gaze at) the object for about 200 ms to 350 ms. In this case, if the calculation cycle of the eye gaze position is e.g. 1 ms, there is a tendency that about 200 to 350 eye gaze positions are comparatively close to each other. The eye gaze positions P4 to P7 tend to have a high likelihood of being eye gaze positions when the user S is gazing at something. At this time, if an object as a target of a gaze by the user S besides the commodity Ct does not exist around the commodity Ct, the eye gaze positions P4 to P7 tend to have a high likelihood of being eye gaze positions when the user S is gazing at the commodity Ct. For example, if an object other than the commodity Ct does not exist on the commodity shelf 200 as illustrated in FIG. 18, the possibility that the user S is gazing at e.g. a blank space above the commodity shelf 200 is low. Therefore, the eye gaze positions P4 to P7 have a high likelihood of being eye gaze positions when the user S is gazing at the commodity Ct (the possibility that the plural eye gaze positions P4 to P7 do not correspond to the position of the commodity Ct due to an error in the calculation of the eye gaze positions P4 to P7 is high).

In that regard, according to the processing illustrated in FIG. 19, only eye gaze positions comparatively close to each other are extracted, which allows extraction of only plural eye gaze positions having a high likelihood of being eye gaze positions when the user S is gazing at the commodity Ct. As a result, the accuracy of the correction value can be further enhanced.

In the processing illustrated in FIG. 19, the cluster in which the number of included eye gaze positions is the largest is selected in the step S1906. However, instead of this, a cluster in which the number of included eye gaze positions is equal to or larger than a given threshold may be selected. The given threshold may correspond to the number of eye gaze positions obtained in a period of 200 ms. This is because, generally when a person gazes at an object, the person tends to look at the object for at least about 200 ms as described above. This can accurately extract only eye gaze positions when the user S is gazing at something. If plural clusters in which the number of included eye gaze positions is equal to or larger than the given threshold exist, the correction value calculating unit 12 may execute the processing of the step S902 and the subsequent steps for each of the plural clusters. Such extraction of plural clusters possibly occurs when the user S is gazing at the given object (e.g. price tag) existing near the commodity Ct for example.

Furthermore, in the processing illustrated in FIG. 19, the correction value calculating unit 12 selects the cluster closest to the position of the commodity Ct in the step S1910. However, the correction value calculating unit 12 may select a cluster in consideration of the non-gaze-target object position information in the non-commodity position database 15. The non-gaze-target objects are the commodity shelf 200 itself (e.g. frame and so forth), a gap between the commodity Ct and an adjacent commodity, a wall of a shop, a pillar, etc. If plural eye gaze positions in a particular cluster correspond to the position of such a non-gaze-target object, the plural eye gaze positions in this cluster have a high likelihood of corresponding to eye gaze positions when the user S is gazing at the commodity Ct. This is because it is unnatural for the user S to gaze at a non-gaze-target object. In view of this point, the correction value calculating unit 12 may select a cluster having plural eye gaze positions corresponding to the position of a non-gaze-target object around the commodity Ct in the step S1910 for example.

Figure 20A:
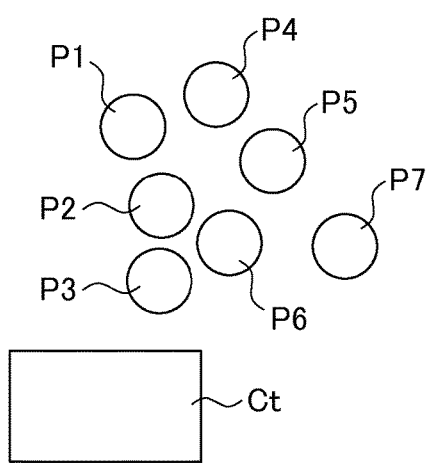
FIGS. 20A and 20B are diagrams illustrating relationship between positional relationship between plural eye gaze positions extracted in a step S1912 and a commodity Ct and necessity for calibration.
Figure 20B:
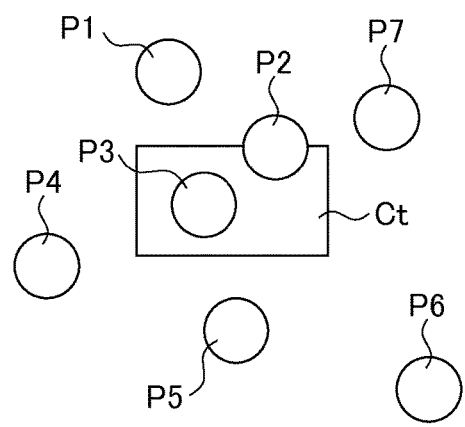

FIGS. 20A and 20B are diagrams illustrating relationship between positional relationship between the plural eye gaze positions extracted in the step S1912 and the commodity Ct and necessity for calibration. In FIGS. 20A and 20B, plural eye gaze positions P1 to P7 and the commodity Ct on the virtual plane M (not illustrated) are schematically illustrated. Suppose that the plural eye gaze positions P1 to P7 are one example of the plural eye gaze positions extracted in the step S1912.

In the example illustrated in FIG. 20A, the plural eye gaze positions P1 to P7 extracted in the step S1912 exist at positions remote from the commodity Ct and have a small spread compared with the example illustrated in FIG. 20B. If the plural eye gaze positions P1 to P7 like those illustrated in the example illustrated in FIG. 20A are extracted in the step S1912, the necessity for calibration is high compared with the example illustrated in FIG. 20B. This is because the plural eye gaze positions P1 to P7 tend to have a high likelihood of being eye gaze positions when the user S is gazing at the commodity Ct as described above. Furthermore, this is because the spread is small and thus the correction value can be calculated with comparatively high accuracy. On the other hand, in the example illustrated in FIG. 20B, the spread is large and the possibility that the correction value can be calculated with comparatively high accuracy is low. In the example illustrated in FIG. 20B, the plural eye gaze positions P1 to P7 are located near the commodity Ct and therefore there is a possibility that the determination result of the step S902 is the positive determination (there is a possibility that the correction value is not calculated).

Next, with reference to FIGS. 21 to 30, a method for covering plural commodities by one eye gaze sensor 20 will be described.

Figure 21:
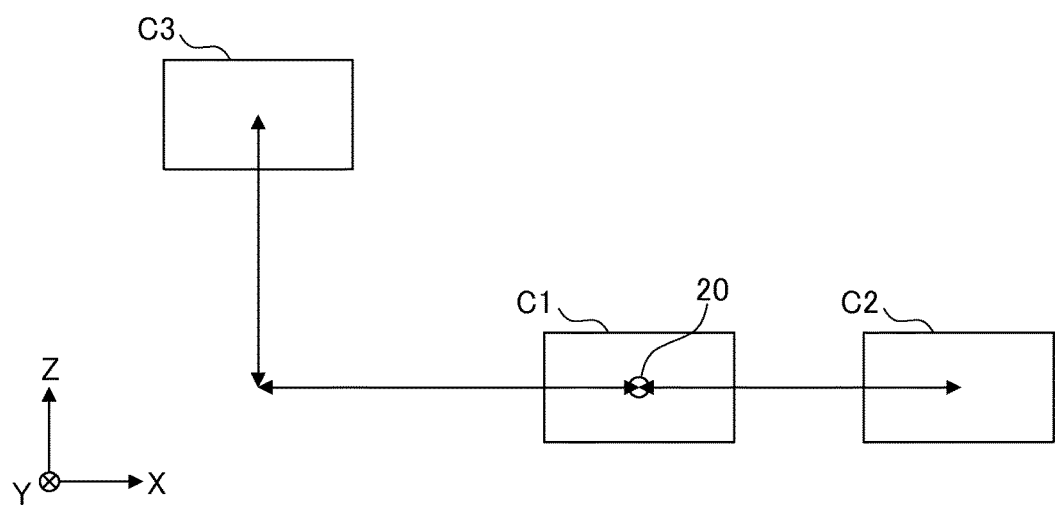
FIG. 21 is a top view illustrating one example of positional relationship among an eye gaze sensor 20 and three commodities C1 to C3.

FIG. 21 is a top view illustrating one example of positional relationship among the eye gaze sensor 20 and three commodities C1 to C3. FIG. 22 is a diagram illustrating one example of data in the commodity position database 14 used in the example illustrated in FIG. 21.

In the example illustrated in FIG. 21, a commodity C1 is disposed at the same position as the eye gaze sensor 20 and a commodity C2 is disposed at a position offset from the eye gaze sensor 20 by x2 in the X-axis direction. Furthermore, a commodity C3 is disposed at a position offset from the eye gaze sensor 20 by −x3 in the X-axis direction and by z3 in the Z-axis direction. In FIG. 22, position information of the respective commodities C1 to C3 when the position of the eye gaze sensor 20 is defined as the origin is represented.

In this case, in the processing illustrated in FIG. 6, the eye gaze position identifying unit 11 calculates eye gaze positions on the virtual plane at Z=0 for the commodity C1 and the commodity C2 and calculates eye gaze positions on the virtual plane at Z=z3 for the commodity C3. Furthermore, in the processing illustrated in FIG. 9, the correction value calculating unit 12 extracts plural eye gaze positions on the virtual plane at Z=0 and plural eye gaze positions on the virtual plane at Z=z3 separately from each other and executes the processing of the step S902 and the subsequent steps separately. Regarding the plural eye gaze positions on the virtual plane at Z=0, there are two commodities as the commodities at which the user S can gaze, i.e. the commodity C1 and the commodity C2. Therefore, in the step S906, the correction value calculating unit 12 may determine which of the commodity C1 and the commodity C2 the extracted plural eye gaze positions correspond to. At this time, on the basis of the relationship between the position of the centroid of the extracted plural eye gaze positions and the respective positions of the commodity C1 and the commodity C2, the correction value calculating unit 12 may associate the extracted plural eye gaze positions with the commodity to which the position of the centroid of the extracted plural eye gaze positions is closer.

Figure 23:
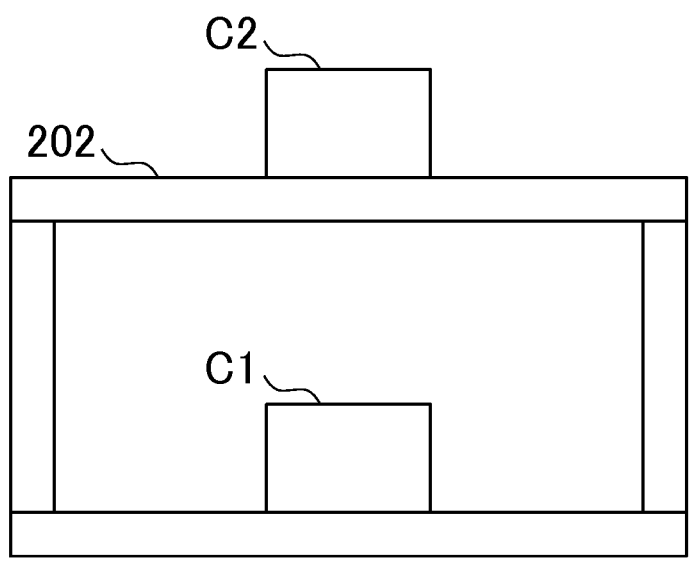
FIG. 23 is a diagram illustrating another example of the assumed scene.

FIG. 23 is a diagram illustrating another example of the assumed scene. In the example illustrated in FIG. 23, two commodities C1 and C2 are disposed on the upper and lower sides of a commodity shelf 202. Here, suppose that the camera 21 of the eye gaze sensor 20 is provided to image the user S who gazes at the commodities C1 and C2. In this case, the camera 21 (not illustrated) is disposed near the commodities C1 and C2 for example and has the eye gaze direction in the positive direction of the Z-axis. Furthermore, suppose that the user S (not illustrated) gazes at the commodities C1 and C2 from a position on the side of the positive direction of the Z-axis relative to the commodities C1 and C2. Moreover, here, it is assumed that the commodity positions of the commodities C1 and C2 have the same Z-coordinate for convenience of avoiding complication of explanation. However, the commodity positions of the commodities C1 and C2 may have different Z-coordinates. Furthermore, with a commodity C3 assumed to exist on the same virtual plane as the other commodities at Z=0, extracted plural eye gaze positions may be associated with the respective commodities.

Figure 24:
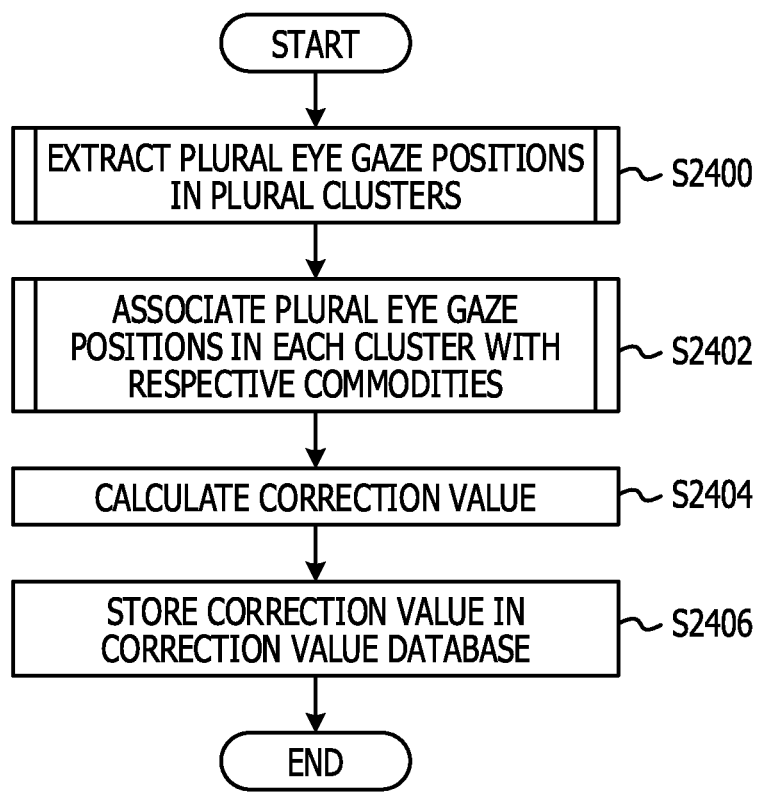
FIG. 24 is a flowchart illustrating another example of the correction value database generation processing executed by the eye gaze position detecting device 100.
Figure 25A:
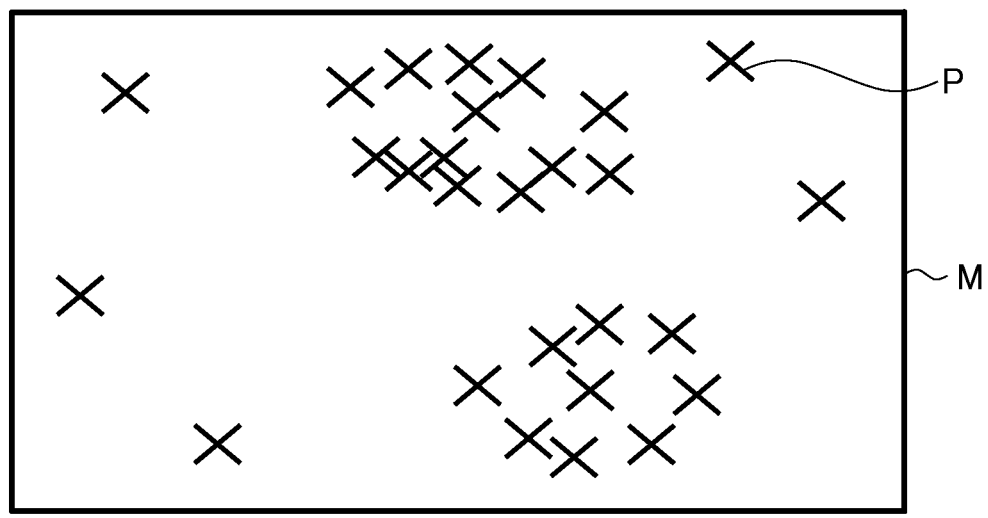
FIGS. 25A and 25B are explanatory diagrams of relationship between clusters and plural eye gaze positions.
Figure 25B:
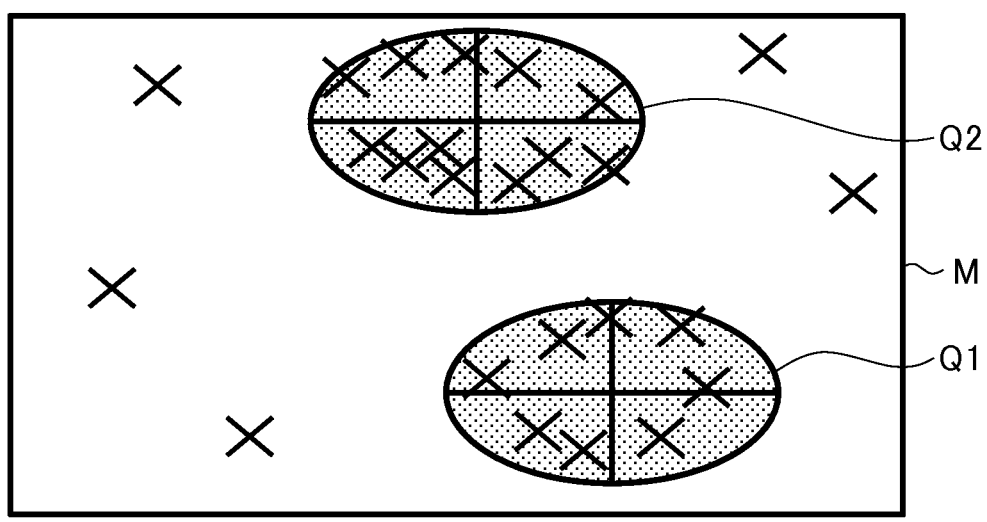
Figure 26:
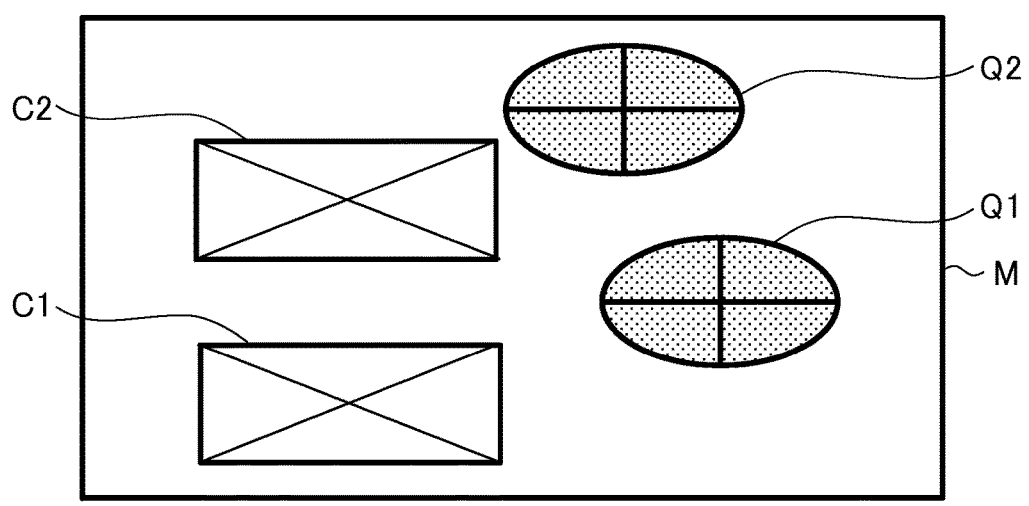
FIG. 26 is a diagram illustrating one example of positional relationship between plural clusters and plural commodities.
Figure 27:
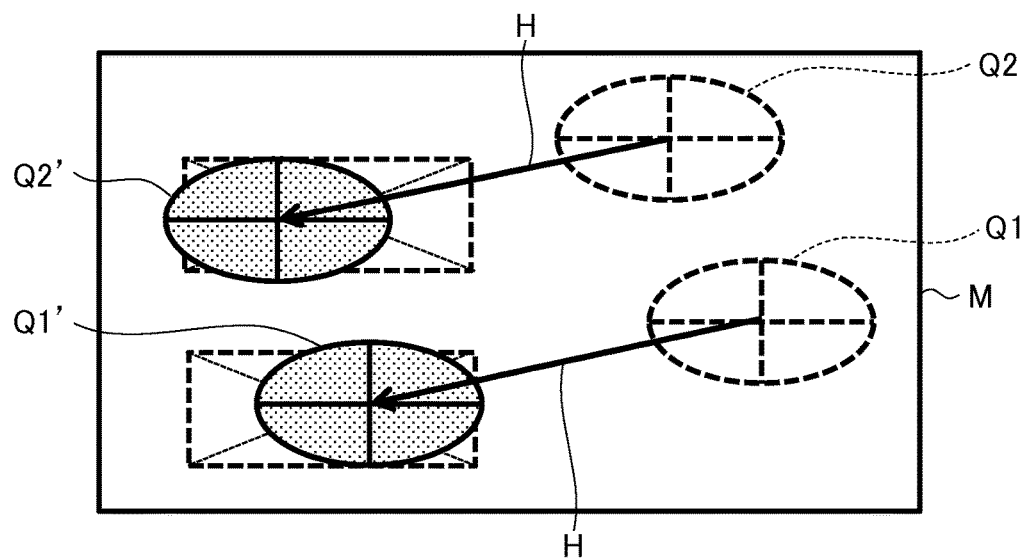
FIG. 27 is an explanatory diagram of a calculation method of a correction value.

FIG. 24 is a flowchart illustrating another example of the correction value database generation processing executed by the eye gaze position detecting device 100. The processing illustrated in FIG. 24 can be applied to the scene illustrated in FIG. 23 for example. In the following, explanatory diagrams of FIGS. 25 to 27 illustrate an example relating to the scene illustrated in FIG. 23.

In a step S2400, the correction value calculating unit 12 extracts plural clusters (along with the clusters, plural eye gaze positions in each cluster). The method thereof will be described later. FIGS. 25A and 25B are explanatory diagrams of relationship between the clusters and the plural eye gaze positions. In FIG. 25A, plural eye gaze positions P on the virtual plane M are represented by cross marks. In FIG. 25B, clusters Q1 and Q2 extracted from the plural eye gaze positions P on the virtual plane M are schematically illustrated.

In a step S2402, the correction value calculating unit 12 associates each cluster (along with each cluster, the plural eye gaze positions in each cluster) with a respective one of the commodities in the commodity position database 14. The correction value calculating unit 12 does not associate the commodity having position information closest to the plural eye gaze positions in a certain cluster with the plural eye gaze positions in this cluster, but carries out the associating on the basis of the relationship between the positional relationship among the clusters and the positional relationship among the commodities. An example of the method of the associating will be described later. For example, in FIG. 26, the clusters Q1 and Q2 and commodity regions relating to the commodities C1 and C2 on the virtual plane M are schematically illustrated. Here, a case is assumed in which the correction value calculating unit 12 could associate plural eye gaze positions in the respective clusters Q1 and Q2 with the commodities C1 and C2, respectively, in the commodity position database 14. If such associating cannot be carried out, the correction value calculating unit 12 may return to the step S2400 and carry out the step S2402 again with change in the clustering method.

In a step S2404, the correction value calculating unit 12 calculates a correction value to cause the plural eye gaze positions in each cluster to match the position of a corresponding one of the commodities. For example, in the scene illustrated in FIG. 23, the correction value calculating unit 12 calculates the correction value to cause the plural eye gaze positions in the cluster Q1 to match the position of the commodity C1 and cause the plural eye gaze positions in the cluster Q2 to match the position of the commodity C2 as illustrated in FIG. 27. The correction value may be a vector H identical between the clusters as illustrated in FIG. 27. In the example illustrated in FIG. 27, the clusters Q1 and Q2 in the case of being moved on the basis of the vector H are represented by symbols Q1' and Q2', respectively. The correction method is arbitrary and the above-described method may be used. For example, the correction value calculating unit 12 may obtain, as the correction value, a movement vector with which each cluster is to overlap with the position of a respective one of the commodities or the position of the centroid of a respective one of the commodities at a higher degree when the respective clusters (circumscribed rectangles, circumscribed circles, the positions of the centroid, or the like) are each moved in the same manner. Alternatively, the correction value calculating unit 12 may obtain, as the correction value, a movement vector with which each cluster is to get closer to the position of a respective one of the commodities or the position of the centroid of a respective one of the commodities when the respective clusters (circumscribed rectangles, circumscribed circles, the positions of the centroid, or the like) are each moved in the same manner. Alternatively, the correction value calculating unit 12 may obtain, as the correction value, a movement vector with which the center or centroid of the circumscribed rectangle or circumscribed circle of each cluster is to be included in a respective one of the commodity regions. Alternatively, the correction value calculating unit 12 may obtain, as the correction value, a movement vector with which the center or centroid of each commodity region is to be included in the circumscribed rectangle or circumscribed circle of a respective one of the clusters. Alternatively, the correction value calculating unit 12 may obtain, as the correction value, a movement vector with which the sum of the respective distances between the center or centroid of each commodity region and the center or centroid of the circumscribed rectangle or circumscribed circle of a respective one of the clusters is to take the minimum value. Alternatively, the correction value calculating unit 12 may calculate the correction value by arbitrarily combining these methods.

In a step S2406, the correction value calculating unit 12 stores the correction value calculated in the step S2404 in the correction value database 18. This processing itself may be the same as the processing of the above-described step S910.

According to the processing illustrated in FIG. 24, it is possible to calculate the correction value even in the case in which the place toward which the eye gaze of the user S would be oriented cannot be identified as one place, such as the case in which there are plural commodities on a commodity shelf as in the scene illustrated in FIG. 23. As a result, calibration by use of the correction value becomes possible (see FIG. 10).

In the processing illustrated in FIG. 24, the correction value calculating unit 12 associates each cluster (along with each cluster, plural eye gaze positions in each cluster) with a respective one of the commodities in the commodity position database 14. However, such associating may be omitted. The correction value calculating unit 12 may obtain the correction value with which the position of each cluster is to overlap with the position of an object at a higher degree or get closer to the position of the object when the positions of the respective clusters are moved in the same manner.

Figure 28:
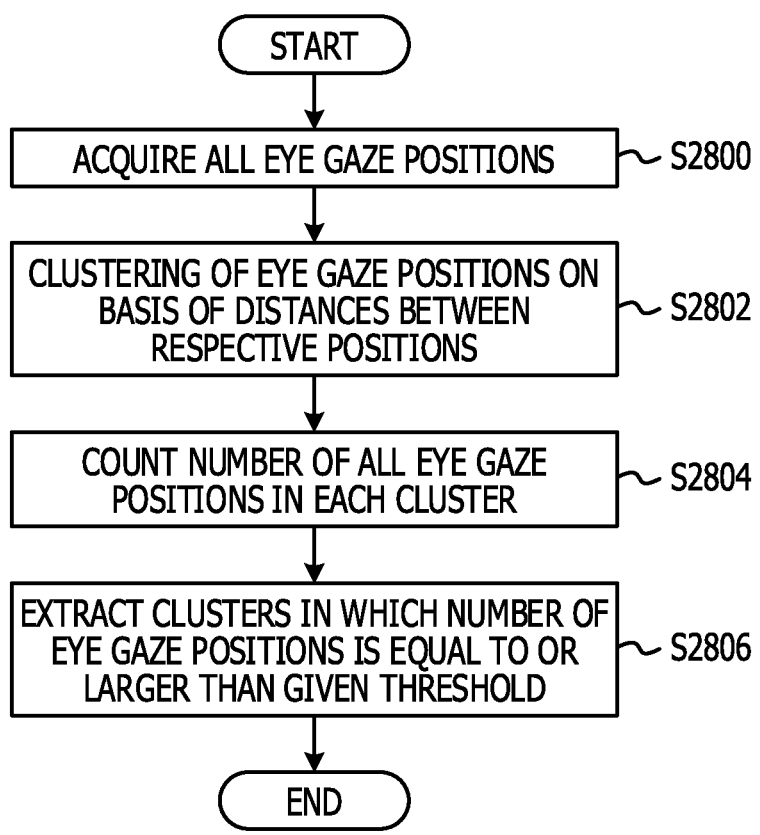
FIG. 28 is a flowchart illustrating another example of the eye gaze position selection processing executed by the correction value calculating unit 12.

FIG. 28 is a flowchart illustrating another example of the eye gaze position selection processing executed by the correction value calculating unit 12. The processing illustrated in FIG. 28 is executed as one example of the processing of the step S2400 illustrated in FIG. 24.

In a step S2800, the correction value calculating unit 12 extracts plural eye gaze positions relating to the same user S from the eye gaze position database 13 as initial extraction.

In a step S2802, the correction value calculating unit 12 carries out clustering of all eye gaze positions extracted in the step S2800 as the initial extraction on the basis of the respective positions. The processing of the step S2802 may be the same as the processing of the above-described step S1902.

In a step S2804, about plural clusters obtained by the clustering in the step S2802, the correction value calculating unit 12 counts the number of eye gaze positions in each cluster, i.e. the numbers of eye gaze positions forming the respective clusters.

In a step S2806, the correction value calculating unit 12 extracts clusters in which the number of included eye gaze positions is equal to or larger than a given threshold on the basis of the count result in the step S2804. If the number of clusters to be extracted is decided in advance, the correction value calculating unit 12 extracts the decided number of clusters from plural clusters in which the number of eye gaze positions is equal to or larger than the given threshold in decreasing order of the number of included eye gaze positions from the cluster with the largest number of eye gaze positions. For example, in the scene illustrated in FIG. 23, the correction value calculating unit 12 extracts two clusters from plural clusters in which the number of eye gaze positions is equal to or larger than the given threshold in decreasing order of the number of included eye gaze positions from the cluster with the largest number of eye gaze positions.

According to the processing illustrated in FIG. 28, as with the processing illustrated in the above-described FIG. 19, only eye gaze positions comparatively close to each other are extracted, which allows extraction of only plural eye gaze positions having a high likelihood of being eye gaze positions when the user S is gazing at a commodity. Furthermore, according to the processing illustrated in FIG. 28, it is possible to extract plural clusters each including plural eye gaze positions having a high likelihood of being eye gaze positions when the user S is gazing at a commodity.

In the processing illustrated in FIG. 28, the clustering of plural eye gaze positions is carried out on the basis of the eye gaze positions. However, the processing is not limited thereto. For example, the correction value calculating unit 12 may refer to the times when the plural eye gaze positions have been acquired and extract only eye gaze positions having a high likelihood of being eye gaze positions when the user S is gazing at a commodity on the basis of the time-sequential movement and speed of the eye gaze positions. For example, if an eye gaze position acquired at a certain time and an eye gaze position acquired in a given time from the time are within a given distance, the correction value calculating unit 12 determines that the user S was gazing at the vicinity of the eye gaze positions (looking at any commodity). In this case, the correction value calculating unit 12 may carry out clustering with use of these eye gaze positions. On the other hand, if an eye gaze position acquired at a certain time and an eye gaze position acquired in a given time from the time are not within a given distance, the correction value calculating unit 12 determines that these eye gaze positions are not eye gaze positions when the user S is gazing at something (are not eye gaze positions when the user S is looking at a commodity). In this case, the correction value calculating unit 12 may discard these eye gaze positions and carry out clustering with use of other eye gaze positions.

Figure 29:
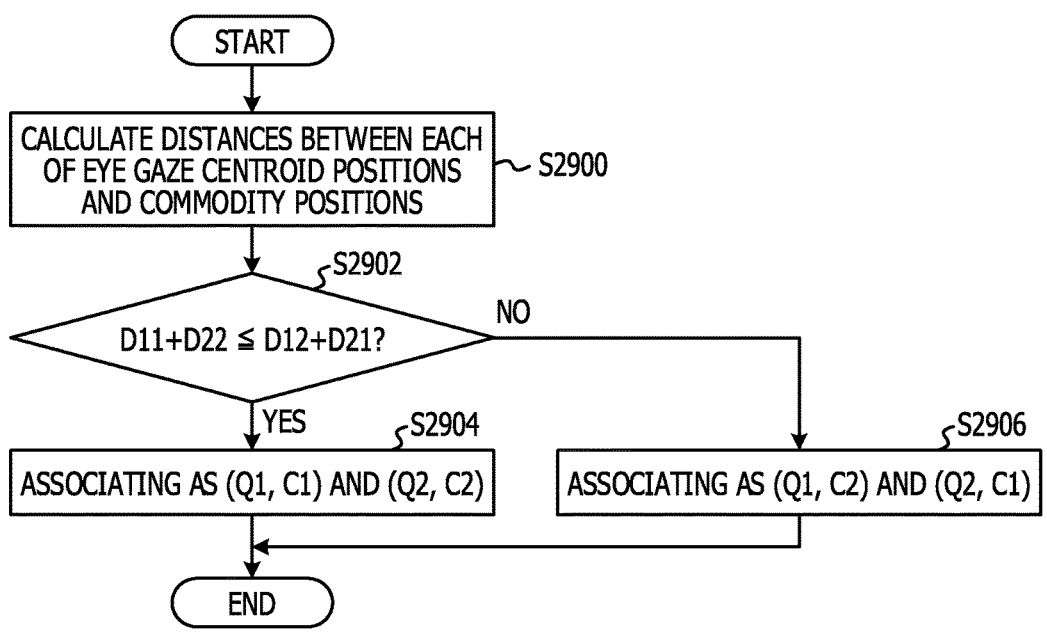
FIG. 29 is a flowchart illustrating one example of associating processing.

FIG. 29 is a flowchart illustrating one example of associating processing. The processing illustrated in FIG. 29 is executed as one example of the processing of the step S2402 illustrated in FIG. 24. In the following, a case is assumed in which plural eye gaze positions relating to two clusters are extracted in the scene illustrated in FIG. 23. Here, the two clusters are referred to as a first cluster Q1 and a second cluster Q2.

Figure 30:
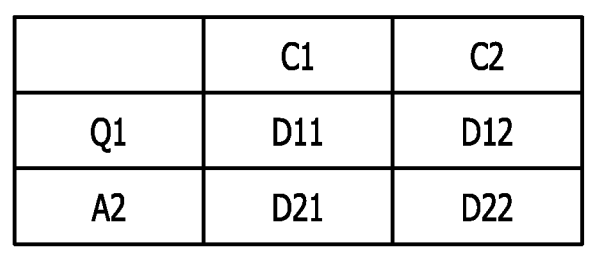

In a step S2900, the correction value calculating unit 12 calculates the positions of the centroid of the plural eye gaze positions that are extracted in the step S900 and relate to the first cluster Q1 and the second cluster Q2 on each cluster basis. Furthermore, the correction value calculating unit 12 refers to the commodity position database 14 and calculates the respective distances D11, D12, D21, and D22 between each of the first cluster Q1 and the second cluster Q2 and the respective positions of the commodities C1 and C2. As represented in FIG. 30, the distance D11 is the distance between the position of the centroid relating to the first cluster Q1 and the commodity C1 and the distance D12 is the distance between the position of the centroid relating to the first cluster Q1 and the commodity C2. Furthermore, the distance D21 is the distance between the position of the centroid relating to the second cluster Q2 and the commodity C1 and the distance D22 is the distance between the position of the centroid relating to the second cluster Q2 and the commodity C2.

In a step S2902 to a step S2906, the correction value calculating unit 12 refers to the commodity correspondence rule database 16 and associates the plural eye gaze positions extracted in the step S900 with commodities in the commodity position database 14. Here, suppose that a relational expression like one represented in the step S2902 is stored in the commodity correspondence rule database 16.

For example, in the step S2902, the correction value calculating unit 12 determines whether or not the distances D11, D12, D21, and D22 calculated in the step S2900 satisfy a relationship of D11+D22≤D12+D21. If the relationship of D11+D22≤D12+D21 is satisfied, the processing proceeds to the step S2904. In the other case, the processing proceeds to the step S2906.

In the step S2904, the correction value calculating unit 12 associates the plural eye gaze positions in the first cluster Q1 with the commodity C1 in the commodity position database 14 and associates the plural eye gaze positions in the second cluster Q2 with the commodity C2 in the commodity position database 14.

In the step S2906, the correction value calculating unit 12 associates the plural eye gaze positions in the first cluster Q1 with the commodity C2 in the commodity position database 14 and associates the plural eye gaze positions in the second cluster Q2 with the commodity C1 in the commodity position database 14.

According to the processing illustrated in FIG. 29, even in the scene in which the two commodities C1 and C2 like those illustrated in FIG. 23 are disposed on the upper and lower sides, the plural eye gaze positions in each cluster can be accurately associated with either one of the two commodities C1 and C2.

Although the scene in which the two commodities C1 and C2 like those illustrated in FIG. 23 are disposed on the upper and lower sides is assumed in the processing illustrated in FIG. 29, this processing can be similarly applied also to a scene in which the two commodities C1 and C2 are disposed on the left and right sides. Furthermore, this processing can be applied also to a scene in which three or more commodities are disposed in the upward-downward direction or the left-right direction.

Moreover, in the processing illustrated in FIG. 29, the correction value calculating unit 12 determines whether or not the relationship of D11+D22≤D12+D21 is satisfied in the step S2902. However, the associating may be carried out by another method. For example, the correction value calculating unit 12 may associate the first cluster Q1 and the second cluster Q2 with the commodities C1 and C2 if the distance between the position of the centroid relating to the first cluster Q1 and the position of the centroid relating to the second cluster Q2 substantially corresponds with the distance between the commodity C1 and the commodity C2. In this case, the correction value calculating unit 12 may associate the cluster with the larger Y-coordinate of the position of the centroid in the first cluster Q1 and the second cluster Q2 with the commodity C2 and associate the cluster with the smaller Y-coordinate with the commodity C1.

Although the respective embodiments are described in detail above, the disclosed techniques are not limited to a particular embodiment and various modifications and changes can be made in the range set forth in the scope of claims. Furthermore, it is also possible to combine all or a plurality of constituent elements of the above-described embodiments.

For example, although a person is assumed as the user S in the above-described explanation, the user S may be an animal other than the human, such as a gorilla or a monkey.

Furthermore, in the above-described embodiments, the correction value calculating unit 12 calculates the correction value by using plural eye gaze positions about each of the users S in order to consider the individual difference of each of the users S. However, the correction value calculating unit 12 may calculate the correction value by using plural eye gaze positions relating to plural users S. This allows a correction value calculated by using plural eye gaze positions relating to a certain user S to be used in calculation of an eye gaze position relating to another user S, which can increase the opportunities to use the correction value. However, in the configuration to calculate the correction value about each of the users S, the calibration processing unit 11b may carry out correction regarding a new user S by using a correction value relating to another user S until a correction value relating to this new user S is calculated by the correction value calculating unit 12.

Moreover, although an object as a gaze target of the user S is a commodity in the above-described explanation, a gaze target may be an object other than the commodity (object that does not become a target of a business transaction). For example, an object as a gaze target of the user S may be a poster, an advisement, a painting, a sculpture, an image, a building, etc. In addition, an object as a gaze target of the user S may be content displayed on a screen of a display, a portable terminal, a wearable terminal, etc.

Furthermore, although an object as a gaze target of the user S is a commodity that can be displayed on a commodity shelf in the above-described explanation, the size, shape, and so forth of the commodity are arbitrary and the display method of the commodity is also arbitrary.

Moreover, although the virtual plane M includes the position (coordinates) of the object as the gaze target of the user S in the above-described explanation, the virtual plane M does not necessarily need to include the position (Z-coordinate) of a commodity based on the commodity position database 14. For example, the virtual plane M may be set to include a position offset from the position (Z-coordinate) of a commodity based on the commodity position database 14 by a given value in the Z-axis positive direction. The given value may be half the length of the commodity in the Z-direction, or the like.

In addition, although the virtual plane M is a vertical plane in the above-described explanation, the virtual plane M may be inclined relative to a vertical plane.

Furthermore, in the above-described embodiments, eye gaze positions calculated by the eye gaze position identifying unit 11 are stored (accumulated) in the eye gaze position database 13 and the correction value calculating unit 12 brings out plural eye gaze positions from the eye gaze position database 13. However, the configuration is not limited thereto. For example, the eye gaze position detecting device 100 may include a database to store (accumulate) eye gaze vectors acquired by the eye gaze vector acquiring unit 10 and the eye gaze position identifying unit 11 may bring out plural eye gaze vectors from the database to collectively calculate plural eye gaze positions. In this case, the correction value calculating unit 12 may execute the above-described processing by using plural eye gaze positions collectively calculated by the eye gaze position identifying unit 11 (another example of the first or second plural eye gaze positions).

In addition, in the above-described embodiments, the eye gaze position identifying unit 11 calculates (identifies) the eye gaze position from the eye gaze vector. However, the eye gaze position may be acquired by an arbitrary method and the processing of calculating the eye gaze position from the eye gaze vector acquiring unit and the eye gaze vector is one mode of the method for acquiring the eye gaze position.

Moreover, in the above-described embodiments, the correction value calculating unit 12 calculates the correction value to cause plural eye gaze positions to match the position of a commodity in both the X-direction and the Y-direction. However, the correction value calculating unit 12 may calculate a correction value to cause plural eye gaze positions to match the position of a commodity in only either one of the X-direction and the Y-direction. For example, in a scene like that illustrated in FIG. 11, if not one but plural commodities Ct are arranged in the X-direction, it is often difficult to determine which commodity Ct in the X-direction the user S is gazing at. In this case, the correction value calculating unit 12 may calculate a correction value to cause plural eye gaze positions to match the position of a commodity in only the Y-direction.]

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An eye gaze detection device comprising:
   a memory configured to store position information regarding object positions where objects being displayed are located; and
   a processor coupled to the memory and configured to:
   specify a plurality of eye gaze positions regarding a subject captured in each of a plurality of images,
   determine a first object from among the objects in accordance with at least a part of the plurality of eye gaze positions and the position information, and
   calculate a correction value based on both a first object position regarding the first object and a location representing first eye gaze positions included in the plurality of eye gaze positions, the correction value causing the location to match the first object position,
   wherein the processor is configured to identify each of eye gaze vectors from each of the plurality of images, and calculates the plurality of eye gaze positions in accordance with each of the eye gaze vectors, the plurality of eye gaze positions being with reference to a virtual space where the objects are located, and
   the virtual space includes the object positions of the objects indicated by the position information.

2. The eye gaze detection device according to claim 1, wherein the correction value is an amount of offset between the location and the first object position.

3. The eye gaze detection device according to claim 1, wherein the correction value is a transformation matrix to transform the location into the first object position.

4. The eye gaze detection device according to claim 1, wherein
   the first eye gaze positions are determined in accordance with a region including the first eye gaze positions, a shape and size of the region being similar or identical to a shape and size of a first object region associated with the first object.

5. The eye gaze detection device according to claim 1, wherein the processor is configured to:
   carry out a clustering process for clustering the plurality of eye gaze positions, and
   select a cluster including the first eye gaze positions, the cluster including a largest number of eye gaze positions from among a plurality of clusters obtained by the clustering process.

6. The eye gaze detection device according to claim 1, wherein
   the first object is determined by comparing a shape or size of a first object region associated with the first object with a shape or size of a region including the part of the plurality of eye gaze positions, the part of the plurality of eye gaze positions being determined in accordance with distances between each of the plurality of eye gaze positions.

7. The eye gaze detection device according to claim 1, wherein the processor is configured to identify new eye gaze positions of the subject by correcting the first eye gaze positions based on the correction value.

8. The eye gaze detection device according to claim 1, wherein the first object is an item displayed on a commodity shelf.

9. An eye gaze detection method executed by a computer, the eye gaze detection method comprising:
   specifying a plurality of eye gaze positions regarding a subject captured in each of a plurality of images;
   referring to a memory that stores position information regarding object positions where objects being displayed are located;
   determining a first object from among the objects in accordance with at least a part of the plurality of eye gaze positions and the position information; and
   calculating a correction value based on both a first object position regarding the first object and a location representing first eye gaze positions included in the plurality of eye gaze positions, the correction value causing the location to match the first object position; and identifying each of eye gaze vectors from each of the plurality of images, and calculating the plurality of eye gaze positions in accordance with each of the eye gaze vectors, the plurality of eye gaze positions being with reference to a virtual space where the objects are located, wherein the virtual space includes the object positions of the objects indicated by the position information.

10. An eye gaze detection device comprising:

a memory configured to store position information regarding object positions where objects being displayed are located; and a processor coupled to the memory and configured to:

acquire a plurality of eye gaze directions of a subject, the plurality of eye gaze directions being identified from a plurality of images respectively, generate a plurality of eye gaze positions by identifying an eye gaze position for each of the plurality of eye gaze directions, the plurality of eye gaze positions corresponding to intersections of a virtual plane and the each of the plurality of eye gaze directions, and the virtual plane being set based on a three-dimensional position at which the subject is assumed to gaze, determine a first object from among the objects in accordance with at least a part of the plurality of eye gaze positions and the position information, identify a location of a virtual region that includes first eye gaze positions included in the plurality of eye gaze positions, when it is detected that the virtual region has a shape and size tbat4s similar or identical to a shape and size associated with the first object, calculate a correction value to be applied when a new eye gaze position is identified from a new image based on the location of the virtual region, and a first object position of the first object, and identify each of eye gaze vectors from each of the plurality of images, and calculate the plurality of eye gaze positions in accordance with each of the eye gaze vectors, the plurality of eye gaze positions being with reference to a virtual space where the objects are located, wherein the virtual space includes the object positions of the objects indicated by the position information.

* * * * *